United States Patent [19]

Primeau et al.

[11] Patent Number: 5,187,168
[45] Date of Patent: Feb. 16, 1993

[54] SUBSTITUTED QUINAZOLINES AS ANGIOTENSIN II ANTAGONISTS

[75] Inventors: John L. Primeau, Princeton; Lloyd M. Garrick, Plainsboro, both of N.J.

[73] Assignee: American Home Products Corporation, New York, N.Y.

[21] Appl. No.: 782,850

[22] Filed: Oct. 24, 1991

[51] Int. Cl.⁵ ............ A61K 31/505; C07D 239/14
[52] U.S. Cl. .................... 514/259; 514/260; 514/258; 544/278; 544/280; 544/283; 544/284; 544/286; 544/291; 544/292; 544/295
[58] Field of Search ........ 544/285, 284, 286, 291, 544/292, 293; 514/259, 260

[56] References Cited

U.S. PATENT DOCUMENTS 4,880,804 11/1989 Carini et al. .................. 514/2345

FOREIGN PATENT DOCUMENTS 0401030 12/1990 European Pat. Off.
0411766A 2/1991 European Pat. Off.
0412848A 2/1991 European Pat. Off.
0419048 3/1991 European Pat. Off.

OTHER PUBLICATIONS

Can. J. Chem. 1984, 62, 2575 Only Page 2575 Provided.
Chem. Abst. vol. 111, 232719e (1989).
Jour. Cell Biology, vol. 117(1) 157, 1992.

Primary Examiner—John M. Ford
Assistant Examiner—Jyothsna Venkat
Attorney, Agent, or Firm—Walter Patton

[57] ABSTRACT

There are disclosed compounds of the general formula I:

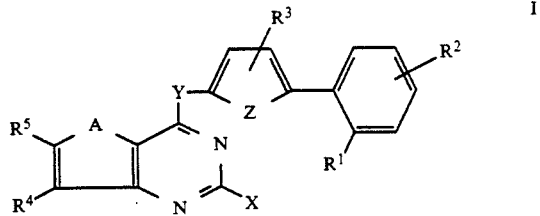

wherein
A is $-CR^7=CR^8-$;
Z is $-CR^7=CR^8-$;
X is H, $NR^9R^{10}$, $OR^{11}$, CN, F, Cl, I, Br, perfluoroalkyl, alkyl,alkoxy, alkyl-OH, alkoxyalkyl, $-(CH_2)_nCO_2R^{11}$, $-(CH_2)_nCONR^9R^{10}$;
Y is $NR^{13}$, $NR^{13}CR^{12}R^{14}$, $CR^{12}R^{14}NR^{13}$;
$R^1$ is 5-tetrazolyl, $CO_2R^{11}$, $SO_3H$, $NHSO_2CH_3$, $NHSO_2CF_3$;
$R^2,R^3,R^4,R^7R^8$ is H, alkyl, alkoxy, alkoxyalkyl, alkyl-OH, perfluoroalkyl, aralkyl, CN, $NO_2$, $SO_2R^{13}$, $-(CH_2)_nCO_2R^{11}$, $-(CH_2)_nCONR^9R^{10}$, $OR^{11}$, F,Cl,Br,I, $NR^9R^{10}$;
$R^5$ is alkyl, alkoxy, alkoxyalkyl, alkyl-OH, perfluoroalkyl, aralkyl, H, $-CN$, $NO_2$, $SO_2R^{13}$, $-(CH_2)_nCO_2R^{11}$, $-(CH_2)_nCONR^9R^{10}$, $-OH$, $OR^{11}$, F,Cl,Br,I, $NR^9R^{10}$;
$R^9,R^{10}$ is H, alkyl, alkoxyalkyl, alkyl-OH, perfluoroalkyl, aralkyl;
$R^{11}$ is H, alkyl, aralkyl, alkoxyalkyl;
$R^{12},R^{14}$ is H, alkyl, alkoxy, alkoxyalkyl, alkyl-OH, perfluoroalkyl, aralkyl, CN, $NO_2$, $SO_2R^{13}$, $-(CH_2)_nCO_2R^{11}$, $-(CH_2)_nCONR^9R^{10}$;
$R^{13}$ is H, $OR^{11}$, alkyl, perfluoroalkyl, aralkyl, $-(CH_2)_nCO_2R^{11}$, $-(CH_2)_nCONR^9R^{10}$;

wherein alkyl is defined as 1-8 carbons, branched or straight chain; perfluoroalkyl is defined as 1-6 carbons; aralkyl is defined as 7-12 carbons or 7-12 carbons substituted with fluorine, bromine or chlorine and the phamaceutically acceptable salts, solvates and hydrates thereof, which by virtue of their ability to antagonize angiotensin II are useful for the treatment of hypertension and congestive heart-failure. The compounds are also useful for reducing lipid levels in the blood plasma and are thus useful for treating hyperlipidemia and hypercholesterolemia. Also disclosed are processes for the production of said compounds and pharmaceutical compositions containing said compounds.

35 Claims, No Drawings

SUBSTITUTED QUINAZOLINES AS ANGIOTENSIN II ANTAGONISTS

BACKGROUND OF THE INVENTION

The compounds described in this invention as well as their non-toxic salts and pharmaceutical compositions containing them are useful for the treatment of hypertension and congestive heart failure. These compounds are also useful as lipid lowering agents.

The renin-angiotensin system plays a well-defined role in cardiovascular homeostasis [Ocain, T. D. et al. (1991) Drugs of the Future 16, 37-51]. Angiotensinogen is converted to angiotensin I by the enzyme renin. Angiotensin I is then acted upon by angiotensin converting enzyme (ACE) to form Angiotensin II (A II). A II possesses many crucial properties including vasoconstriction, aldosterone release, and water retention and is implicated as the cause of high blood pressure in a number of species including man. These hypertensive responses are the result of A II acting at specific receptor sites. Compounds which are able to compete with A II for these receptor sites but do not elicit agonistic receptor responses can be expected to counteract (antagonize) the hypertensive effects of A II.

PRIOR ART

E. E. Allen et al describe 4-oxo-quinazolines in EP 0411766 A.

D. A. Roberts et al describe quinoline ethers in EP 0412848 A.

D. J. Carini et al in U.S. Pat. No. 4,880,804 describe N-substituted benzimidazoles. P. Chakravarty et al disclose similar imidazole structures in EP 0401030 A where the phenyl aromatic ring is replaced by a seven membered heterocycle.

E. E. Allen et al disclose N-substituted oxopyrimidines in EP 0419048 A.

Similar structures are reported in EP 0424317 A by P. Herold et al.

Our invention differs from the above mentioned prior art in that we disclose non-peptidic amino substituted nitrogenous 6 membered heterocycles fused to 5 or 6 membered aromatic rings. The non-peptidic A II antagonists disclosed in the above mentioned prior art are either oxo-quinazolines, quinoline ethers, benzimidazoles, fused heterocyclic imidazoles or oxo-pyrimidines.

DESCRIPTION OF INVENTION

This invention describes the composition and utility of novel heterocycles of the general formula I:

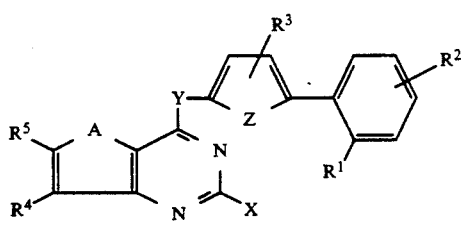

wherein
A is O, S, $NR^6$, $-CR^7=CR^8-$;
Z is O, S, $NR^6$, $-CR^7=CR^8-$;
X is H, $NR^9R^{10}$, $OR^{11}$, CN, F, Cl, I, Br, perfluoroalkyl, alkyl, alkoxy, alkyl-OH, alkoxyalkyl, $-(CH_2)_nCO_2R^{11}$, $-(CH_2)_nCONR^9R^{10}$;

with the provisio that when $Z=-CR^7=CR^8-$ then Y is $NR^{13}$, $NR^{13}CR^{12}R^{14}$, $CR^{12}R^{14}NR^{13}$;
with the provisio that when $Z=O$, S, $NR^6$ then Y is $NR^{13}CR^{12}R^{14}$;
$R^1$ is 5-tetrazolyl, $CO_2R^{11}$, $SO_3H$, $NHSO_2CH_3$, $NHSO_2CF_3$;
$R^2$, $R^3$, $R^4$, $R^7$, $R^8$ is H, alkyl, alkoxy, alkoxyalkyl, alkyl-OH, perfluoroalkyl, aralkyl, CN, $NO_2$, $SO_2R^{13}$, $-(CH_2)_nCO_2R^{11}$, $-(CH_2)_nCONR^9R^{10}$, $OR^{11}$, F, Cl, Br, I, $NR^9R^{10}$;
with the provisio that when $A=-CR^7=CR^8-$ then $R^5$ is alkyl, alkoxy, alkoxyalkyl, alkyl-OH, perfluoroalkyl, aralkyl, H, $-CN$, $NO_2$, $SO_2R^{13}$, $-(CH_2)_nCO_2R^{11}$, $-(CH_2)_nCONR^9R^{10}$, $-OH$, $OR^{11}$, F, Cl, Br, I, $NR^9R^{10}$;
with the provisio that when $A=O$, S, $NR^6$ then $R^5$ is alkyl, alkoxy, alkoxyalkyl, alkyl-OH, perfluoroalkyl, aralkyl, H, $-CN$, $NO_2$, $SO_2R^{13}$, $-(CH_2)_nCO_2R^{11}$, $-(CH_2)_nCONR^9R^{10}$;
$R^6$ is H, alkyl, aralkyl;
$R^9$, $R^{10}$ is H, alkyl, alkoxyalkyl, alkyl-OH, perfluoroalkyl, aralkyl;
$R^{11}$ is H, alkyl, aralkyl, alkoxyalkyl;
$R^{12}$, $R^{14}$ is H, alkyl, alkoxy, alkoxyalkyl, alkyl-OH, perfluoroalkyl, aralkyl, CN, $NO_2$, $SO_2R^{13}$, $(CH_2)_nCO_2R^{11}$, $-(CH_2)_nCONR^9R^{10}$;
$R^{13}$ is H, $OR^{11}$, alkyl, perfluoroalkyl, aralkyl, $-(CH_2)_nCO_2R^{11}$, $-(CH_2)_nCONR^9R^{10}$;
n is 0, 1, 2 or 3;
wherein alkyl is defined as 1-8 carbons, branched or straight chain; perfluoroalkyl is defined as 1-6 carbons; aralkyl is defined as 7-12 carbons or 7-12 carbons substituted with fluorine, bromine or chlorine and the pharmaceutically acceptable salts thereof.

A preferred aspect of the present invention are the compounds represented by the general formula I wherein:
A is S, $-CR^7=CR^8-$;
Z is S, $-CR^7=CR^8-$;
X is H, CN, F, Cl, perfluoroalkyl, alkyl, alkyl-OH, alkoxyalkyl, $-(CH_2)_nCO_2R^{11}$, $(CH_2)_nCONR^9R^{10}$;
with the provisio that when $Z=-CR^7=CR^8-$ then Y is $-NR^{13}$, $-NR^{13}CR^{12}R^{14}$;
with the provisio that when $Z=S$, then Y is $NR^{13}CR^{12}R^{14}$;
$R^1$ is 5-tetrazolyl, $CO_2H$, $SO_3H$, $NHSO_2CF_3$;
$R^2$, $R^3$, $R^4$, $R^7$, $R^8=H$, alkyl, alkoxy, alkoxyalkyl, alkyl-OH, perfluoroalkyl, aralkyl, CN, $NO_2$, $SO_2R^{13}$, $-(CH_2)_nCO_2R^{11}$, $-(CH_2)_nCONR^9R^{10}$, $OR^{11}$, F, Cl, Br, I, $NR^9R^{10}$;
with the provisio that when $A=-CR^7=CR^8-$ then $R^5$ is alkyl, alkoxy, alkoxyalkyl, alkyl-OH, perfluoroalkyl, aralkyl, H, $-CN$, $NO_2$, $SO_2R^{13}$, $-(CH_2)_nCO_2R^{11}$, $-(CH_2)_nCONR^9R^{10}$, $-OH$, $OR^{11}$, F, Cl, Br, I, $NR^9R^{10}$;
with the provisio that when $A=S$ then $R^5$ is alkyl, alkoxy, alkoxyalkyl, alkyl-OH, perfluoroalkyl, aralkyl, H, $-CN$, $NO_2$, $SO_2R^{13}$, $-(CH_2)_nCO_2R^{11}$, $-(CH_2)_nCONR^9R^{10}$;
$R^9$, $R^{10}$ is H, alkyl, perfluoroalkyl, aralkyl;
$R^{11}$ is H, alkyl, aralkyl, alkoxyalkyl;
$R^{12}$, $R^{14}$ is H, alkyl, alkoxy, alkoxyalkyl, alkyl-OH, perfluoroalkyl, aralkyl, CN, $NO_2$;
$R^{13}$ is H, $OR^{11}$, alkyl, perfluoroalkyl, aralkyl, $-(CH_2)_nCO_2R^{11}$, $-(CH_2)_nCONR^9R^{10}$;
n is 0, 1, 2 or 3;
wherein alkyl is defined as 1-8 carbons, branched or straight chain; perfluoroalkyl is defined as 1-6 carbons;

aralkyl is defined as 7-12 carbons or 7-12 carbons substituted with fluorine, bromine or chlorine and the pharmaceutically acceptable salts thereof.

A more preferred aspect of the present invention are the compounds represented by the general formula I wherein:
A is —CR$^7$=CR$^8$—, S;
Z is —CR$^7$=CR$^8$—, S
X is H, Cl, perfluoroalkyl, alkyl;
with the provisio that when Z=—CR$^7$=CR$^8$— then Y is —NR$^{13}$, —NR$^{13}$CR$^{12}$R$^{14}$;

R$^{12}$, R$^{14}$ is H, alkyl, alkoxy, alkoxyalkyl, alkyl-OH, perfluoroalkyl, aralkyl;
R$^{13}$ is H, OR$^{11}$, alkyl, perfluoroalkyl, aralkyl;
n is 0, 1, 2 or 3;
wherein alkyl is defined as 1-8 carbons, branched or straightchain; perfluoroalkyl is defined as 1-6 carbons; aralkyl is defined as 7-12 carbons or 7-12 carbons substituted with fluorine, bromine or chlorine and the pharmaceutically acceptable salts thereof.

The following are specific examples of the invention.

Series I

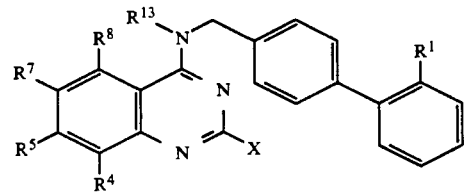

| Example | R$^{13}$ | R$^1$ | R$^8$ | R$^7$ | R$^5$ | R$^4$ | X |
|---|---|---|---|---|---|---|---|
| 4 | H | —CO$_2$Me | H | H | H | H | Cl |
| 10 | H | —CO$_2$H | H | OMe | OMe | H | Cl |
| 26 | H | —CO$_2$Me | H | OMe | OMe | H | HNnBu |
| 22 | H | —CO$_2$Me | H | H | H | H | —HNipentyl |
| 23 | H | —CO$_2$H | H | H | H | H | —HNipentyl |
| 5 | H | —CO$_2$Na | H | H | H | H | Cl |
| 27 | H | —CO$_2$H | H | H | H | H | NH(CH$_2$)$_2$—OMe |
| 28 | H | —CO$_2$H | H | OMe | OMe | H | —NHnBu |
| 29 | H | —CO$_2$Me | H | OMe | OMe | H | —OH |
| 24 | H | CO$_2$Me | H | OMe | OMe | H | OMe |
| 19 | H | CO$_2$Me | H | H | H | H | OH |
| 2 | H | CO$_2$Me | H | Cl | H | H | Cl |
| 3 | H | CO$_2$Na | H | Cl | H | H | Cl |
| 20 | H | CO$_2$H | H | H | H | H | OH |
| 11 | H | CO$_2$H | H | H | H | H | H |
| 30 | H | CO$_2$H | H | H | H | H | —HNnBu |
| 21 | H | CO$_2$Me | H | H | H | H | OAc |
| 7 | H | CO$_2$Me | H | H | H | H | CF$_3$ |
| 8 | H | CO$_2$Na | H | H | H | H | CF$_3$ |
| 6 | H | 5-tetrazolyl | H | H | H | H | CF$_3$ |
| 9 | H | 5-tetrazolyl | H | H | H | H | Cl |
| 1 | H | CO$_2$Na | H | H | Cl | H | CF$_3$ |
| 12 | H | CO$_2$Na | H | H | H | H | CF$_2$CF$_3$ |
| 13 | H | CO$_2$Me | H | H | H | H | CF$_2$CF$_3$ |
| 31 | —CH$_2$—CO$_2$Me | —CO$_2$—CH$_2$CO$_2$—Me | H | H | H | H | CF$_3$ |
| 14 | H | CO$_2$H | H | H | CF$_3$ | H | CF$_3$ |
| 32 | —CH$_2$—CO$_2$H | CO$_2$H | H | H | H | H | CF$_3$ |
| 15 | H | 5-tetrazolyl | H | CH$_3$ | H | H | CF$_3$ |
| 16 | H | 5-tetrazolyl | H | H | H | CH$_3$ | CF$_3$ |
| 17 | H | 5-tetrazolyl | CH$_3$ | H | H | H | CF$_3$ |
| 18a | H | CO$_2$Na | H | H | H | H | CH$_3$ |
| 25 | CH$_3$ | CO$_2$Na | H | H | H | H | CF$_3$ |
| 18b | H | 5-tetrazolyl | H | H | H | H | CH$_3$ | with the provisio that when Z=S, then Y is NR$^{13}$CR$^{12}$R$^{14}$;
R$^1$ is 5-tetrazolyl, CO$_2$H SO$_3$H, NHSO$_2$CF$_3$;
R$^2$, R$^3$, R$^4$, R$^7$, R$^8$ is H, alkyl, alkoxy, alkoxyalkyl, alkyl-OH, perfluoroalkyl, aralkyl, CN, NO$_2$, SO$_2$R$^{13}$, OR$^{11}$, F, Cl, Br, I, NR$^9$R$^{10}$;
with the provisio that when A=—CR$^7$=CR$^8$— then R$^5$ is alkyl, alkoxy, alkoxyalkyl, alkyl-OH, perfluoroalkyl, aralkyl, H, —CN, NO$_2$, SO$_2$R$^{13}$, —OH, OR$^{11}$, F, Cl, Br, I, NR$^9$R$^{10}$;
with the provisio that when A=S then R$^5$ is alkyl, alkoxy, alkoxyalkyl, alkyl-OH, perfluoroalkyl, aralkyl, H, —CN, NO$_2$, SO$_2$R$^{13}$;
R$^9$, R$^{10}$ is H, alkyl, perfluoroalkyl, aralkyl;
R$^{11}$ is H, alkyl, aralkyl, alkoxyalkyl;

SERIES II

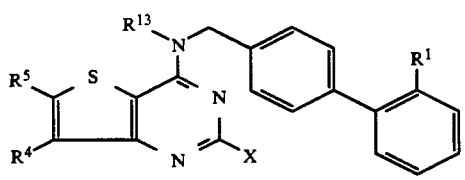

| Example | R$^{13}$ | R$^1$ | R$^5$ | R$^4$ | — | — | X |
|---|---|---|---|---|---|---|---|
| 33 | H | CO$_2$Me | H | H | — | — | Cl |
| 34 | H | CO$_2$Na | H | H | — | — | Cl |
| 35 | H | 5-tetrazolyl | H | H | — | — | CF$_3$ |
| 36 | H | CO$_2$Na | H | H | — | — | CF$_3$ |

SERIES II -continued

| Example | $R^{13}$ | $R^1$ | $R^5$ | $R^4$ | — | — | X |
|---|---|---|---|---|---|---|---|
| 37 | H | 5-tetrazolyl | H | H | — | — | Cl |

SERIES III

| Example | $R^{13}$ | $R^1$ | $R^8$ | $R^4$ | $R^5$ | $R^7$ | X |
|---|---|---|---|---|---|---|---|
| 41 | H | $CO_2Na$ | H | H | H | H | $CF_3$ |

SERIES IV

| Example | $R^{13}$ | $R^1$ | $R^8$ | $R^4$ | $R^5$ | $R^7$ | X |
|---|---|---|---|---|---|---|---|
| 40 | H | $CO_2Na$ | H | H | H | H | $CF_3$ |
| 39 | H | $CO_2Na$ | H | H | H | H | $CF_2CF_3$ |
| 38 | H | $CO_2Me$ | H | H | H | H | $CF_2CF_3$ |

PROCESS OF INVENTION

The compounds of general formula 1 can be prepared as described in scheme 1. The 4-chloroquinazoline 2 can be reacted with the aminomethylbiphenyl 3 in the presence of a base such as sodium acetate or potassium carbonate in tetrahydrofuran or tetrahydrofuran/dioxane at room temperature to reflux. The 2-haloquinazoline 4 (X=Cl) can be converted to 1 by the addition of a nucleophile such as an amine, methanol or water under acid or base cataylsis.

SCHEME 1 wherein $R^1$, $R^4$, $R^5$ and X are as defined above.

Alternately compounds 4 can be prepared as shown in scheme 2. The bromophenylquinazolines 5 can be prepared by reacting the 4-chloroquinazoline with p-bromobenzylamine, followed by protection of the benzylic nitrogen with a suitable protecting group as described by T. W. Greene, *Protective Groups in Organic Synthesis*, John Wiley & Sons, 1981. Conversion of 5 to its Grignard reagent, followed by the reaction of this with the oxazoline shown using the procedure of A. I. Meyers, et. al., *J. Am. Chem. Soc.*, 97, 7383, 1975, yields 6. Conversion of the oxazoline 6 to its corresponding acid, ester and tetrazole can be carried out using the procedures described by Carini et. al. U.S. Pat. No. 4,880,804.

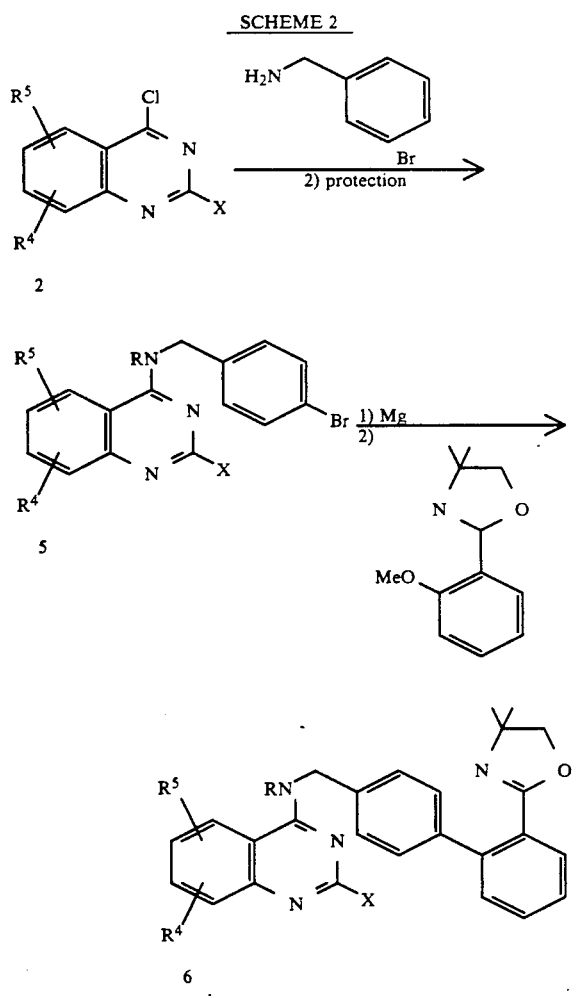

SCHEME 2 wherein $R^4$, $R^5$ and X are as defined above and R is a protecting group.

The preparation of compounds 3 shown in scheme 1 has been disclosed by Carini et. al. U.S. Pat. No. 4,880,804, EP 0324377, EP 0323841, EP 0253310.

The 4-chloroquinazoline 2a (where X=H) can be synthesized as shown in scheme 3. This preparation was described by W. B. Lutz et. al. U.S. Pat. No. 3,266,990.

SCHEME 3

-continued
SCHEME 3

The 4-chloroquinazolines 2b and 2c (where X=Cl and $CF_3$) can be prepared as described in scheme 4. Reaction of the substituted anthranilic acid 7 with urea in refluxing pyridine yields the quinazolinediones 9. Reaction of the analogous anthranilamide 8 with trifluoroacetamide yields the 2-trifluoromethylquinazolones 10a. Reaction of 9 or 10a with $POCl_3$ in the presence of dimethylaniline (DMA) using the procedure reported by T. H. Althius and H. J. Hess (for 9 to 2b where $R^1$=6-OMe and $R^2$=7-OMe); *J. Med. Chem.*, 1977, 20, 146, yields the 4-chloroquinazolines 2b or 2c respectively. Alternately this transformation can be carried out by the procedure described by N. A. Lange et al (for 9 to 2b where R1=R2=H); *J. Amer. Chem. Soc.*, 1930, 52, 3696.

SCHEME 4

-continued
SCHEME 4

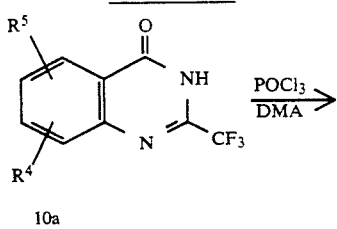

10a

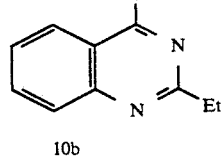

10b

The thienopyrimidine compounds 12 are prepared as shown in scheme 5 using the same reaction conditions as those described in scheme 1.

SCHEME 5

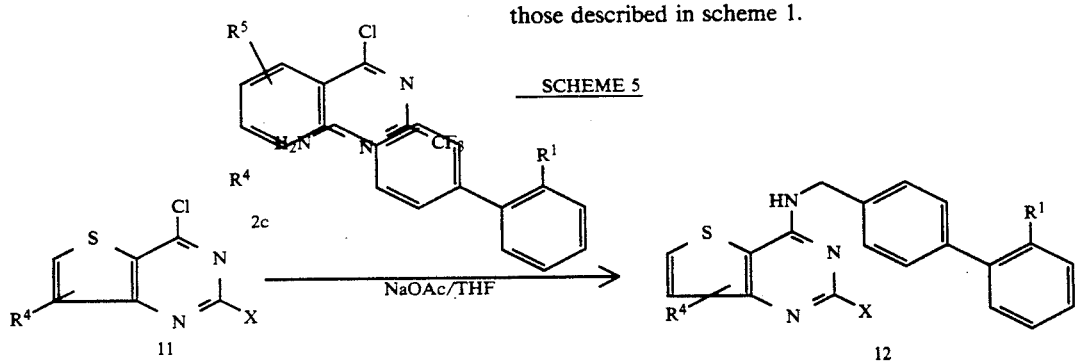

wherein $R^1$, $R^4$ and X are as defined above.

The preparation of the starting 4-chlorothienopyrimidine 11 is described in scheme 6. Reaction of 3-amino-2-carboxamidethiophene with urea led to the thienopyrimidinedione 14. Similar reaction with trifluoroacetamide led to the 2-trifluoromethylpyrimidone 15. These materials were converted to 11a and 11b using POCl₃, catalysed with dimethylaniline (DMA).

SCHEME 6

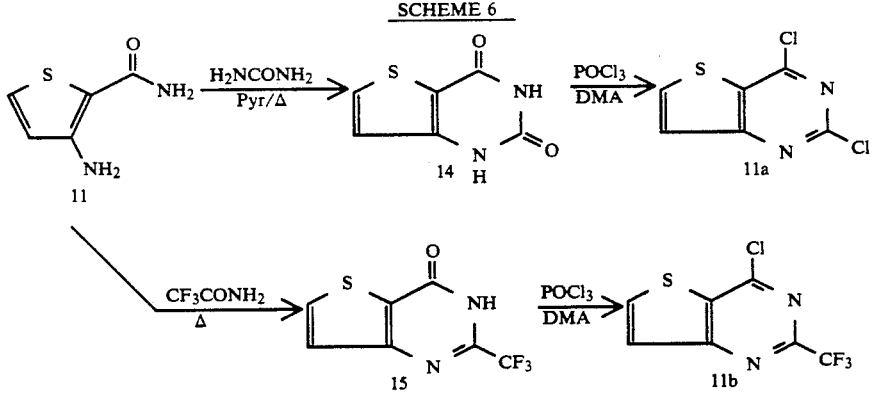

The preparation of 2-methyl-4-chloroquinazoline 2d has been described by E. S. Hand et al; *Can. J. Chem.* 1984, 62, 2570. This procedure can also be used to convert the 2-ethyl-4-quinazolone 10b reported by N. A. Dolgova et al; *Izv. Akad. Nauk. Kaz. SSSR Ser. Khim.*, 1989. #2, 26, to the 4-chloroquinazoline 2e.

Substitution of pentafluoropropanamide for trifluoroacetamide in schemes 4 and 6 leads to the formation of compounds 16 and 17. Using these starting materials in schemes 1 and 5 provides compounds 18 and 19.

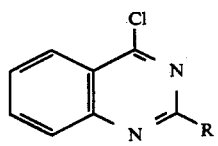

2d, R = Me
2e, R = Et

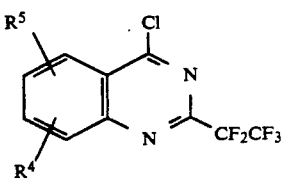

16

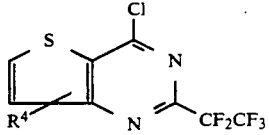

wherein $R^4$, $R^5$ are as defined above.

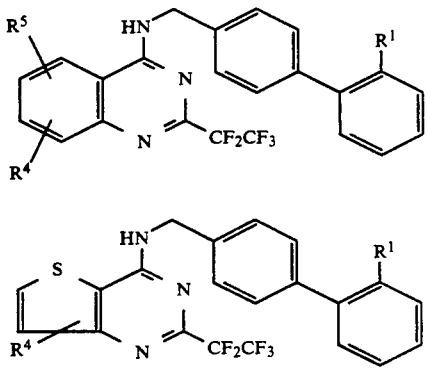

wherein $R^1$, $R^4$, $R^5$ are as defined above.

Replacement of the aminomethylbiphenyl compounds 3 in schemes 1 and 5 with compounds 20 and 21 leads to the formation of the substituted quinazolines 22 and 23, and the substituted thienopyrimidines 24 and 25.

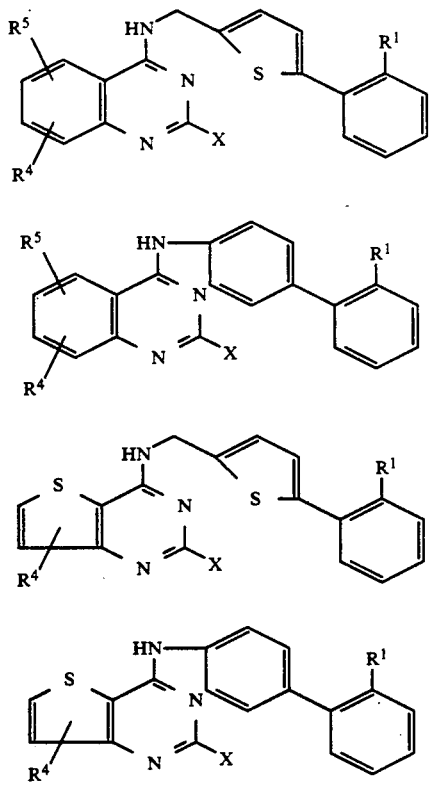

wherein $R^1$, $R^4$, $R^5$ and X are as defined above.

The preparation of this amino ester 20 is described in scheme 7.

SCHEME 7

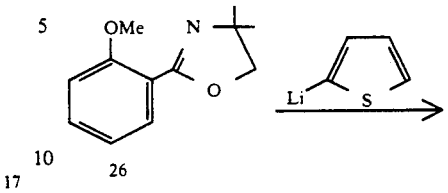

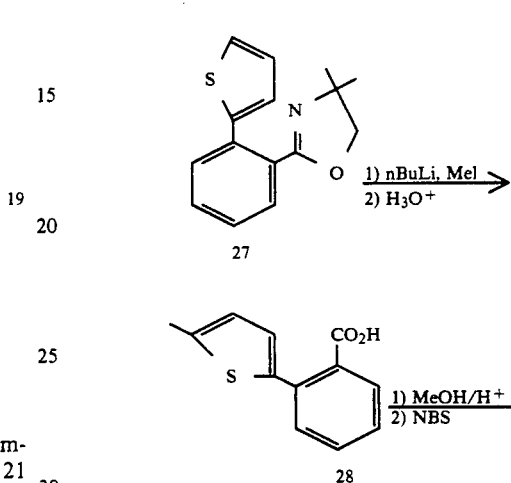

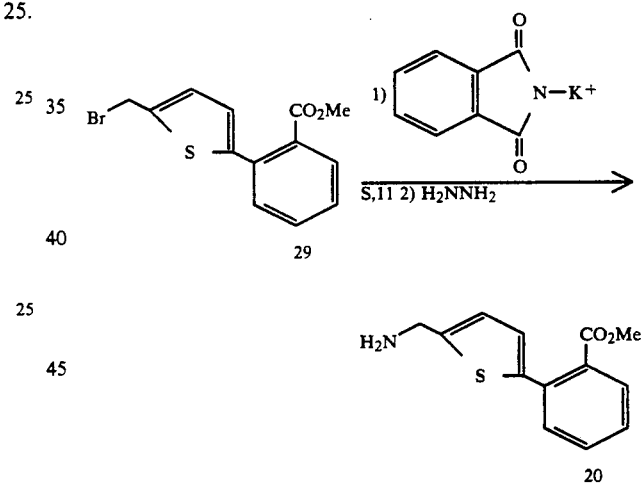

Treatment of the methoxyphenyloxazoline 26 with 2-lithiothiophene leads to the substituted thiophene 27. Methylation using n-BuLi and methyl iodide followed by acid hydrolysis leads to the 2-substituted benzoic acid. Esterification and bromination leads to 29 which is treated under Gabriel conditions to generate the desired amine 20. The amino ester 30 is prepared as illustrated in scheme 8. The commercially available 2-biphenylcarboxylic acid 31 is nitrated using a mixture of concentrated nitric acid in acetic acid (1:19) to yield the nitro-acid 32 previously reported by S. A. Glover et al, *J. Chem. Soc. Perkin I*, 1981, 842. Esterification followed by reduction over palladium yields the desired amino ester 30.

SCHEME 8

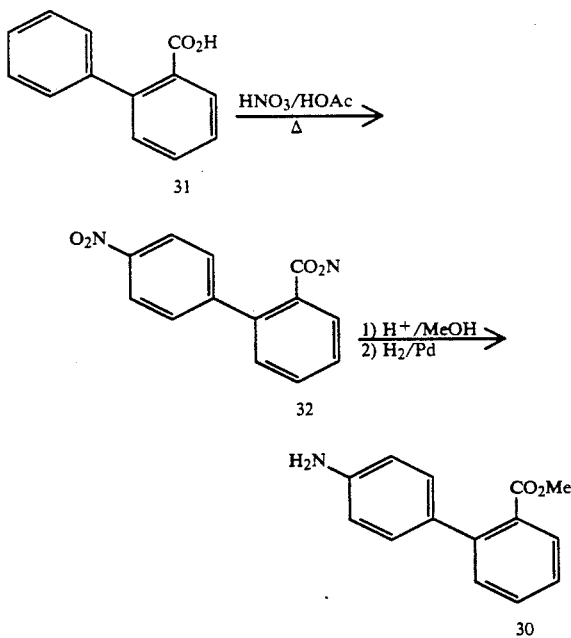

The compounds of this invention may also form salts with inorganic or organic bases. Any pharmaceutically acceptable salts of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. These compounds may also be converted to N-oxides by treatment with hydrogen peroxide by conventional means.

The present invention also provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics, b-blocking agents or ACE inhibitors.

The present invention further provides a compound of the invention for use as an active therapeutic substance. Compounds described in this invention are of particular use in the treatment of hypertension. They can also be used for the treatment of congestive heart-failure. In addition, the compounds of this invention also have therapeutic utility in the treatment of hyperlipidemia, and/or hypercholesterolemia.

The present invention further provides a method of treating hypertension in mammals including man, which comprises administering to the afflicted mammal an antihypertensive effective amount of a compound or a pharmaceutical composition of the invention.

The high affinity of the compounds for the angiotensin II receptor was established using a rat adrenal receptor binding assay, measuring the displacement of radiolabeled angiotensin II from the receptor, described as follows: Anesthetize male Sprague-Dawley rats (300-400 g body weight) with $CO_2$ and sacrifice by cervical dislocation. Dissect adrenal glands and keep in ice-cold sucrose buffer. (0.2M sucrose, 1 mM EDTA, 10 mM Trizma base, pH=7.2). Remove medulla by squashing. Mince the cortex, rinse and homogenize in a chilled ground glass tissue grinder with 15 mL sucrose buffer. Centrifuge at 3000×g for 10 min. (Sorvall RCSC centrifuge, SS34 rotor 6200 rpm). Decant supernatant through gauze. Centrifuge combined supernatants at 12000×g for 13 min. (Beckman ultracentrifuge, 80Ti rotor, 13000 rpm). Centrifuge the supernatant from the previous step at 102000×g for 60 min. (Beckman ultracentrifuge, 80Ti rotor, 38200 rpm). All steps are carried out at 4° C. Resuspend the pellet in 0.5 mL assay buffer (50 mM Tris HCl, 5 mM $MgCl_2$, 0.2% BSA (protease-free), pH=7.4, 25° C.). Store on ice. Determine membrane protein by Lowry or Bradford assay with BSA as standard. The binding assay is performed in triplicate, in 12×75 mm plastic test tubes or in 96-well plate (final volume of 0.25 mL). Add 140 mL assay buffer. Add 10 mL cold A II (to give final concentrations of $10^{-10}$–$10^{-7}$M for standard curve and $10^{-4}$M for nonspecific binding), compounds (e.g., for final concentrations of 25 and 100 mM or 1 mM, 10 nM and 100 nM) in 50% DMSO, or 50% DMSO as a control. Add 50 mL membrane suspension (e.g., 10 mg protein). Preincubate for 30 min at 25° C. Add 50 ml $^{125}$I-A II which has been prepared as shown below (final concentration=1 nM). Incubate for 35 min at 25° C. Stop the incubation by adding 1 mL ice-cold buffer (assay buffer without BSA). Filter with GF/C filters on cell harvester (filters are presoaked in the assay buffer containing 1% polyethyleneimine). Rinse assay tubes 3X with 5 mL cold buffer (assay buffer without BSA). Cut and deposit the filter discs into test tubes and count on gamma counter for 1 min. Adjust the specific activity of $^{125}$I-A II purchased from New England Nuclear to 500 mCi/nmole by adding cold A II in water. Calculate the quantities of hot A II and the cold A II needed and make the dilution. Aliquot, seal tight, and store frozen until needed. Calculate the concentration of the total A II (hot+cold) after dilution. On the day of assay, thaw the frozen aliquot and adjust the volume to give a concentration of 5 pmole/mL (or 0.25 pmole/50 mL) with assay buffer (+protease-free BSA). For final concentration of 1 nM $^{125}$I-A II in the assay, add 50 mL (or 0.25 pmole) per test tube to a final volume of 250 mL. The results of these binding assays are reported as the inhibitory concentration of the test compound necessary to achieve fifty percent displacement of radiolabeled angiotensin II from its receptor ($IC_{50}$), or the percent displacement of binding of A II at its receptor at $10^{-8}$M concentration of test compound (% I). All the examples cited in this invention displayed significant inhibition of A II binding in this assay. Typically these compounds displayed an $IC_{50}$ in this assay of less than or equal to 150 μM.

In accordance with their ability to antagonize angiotensin II, the compounds of this invention show antihypertensive action in the following A II-infused rat model. Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockade is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 mg/kg/min (at 9.6 uL-min). The A II infusion returns arterial pressure to or slightly above the control level. Once arterial pressure has stabilized with the A II infusion, baseline values for mean arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound. For example, the product of Example 36 administered at 10 mg/kg id lowered the A II dependent blood pressure by an average of 45% one half hour post-administration.

As illustrated above the compounds of this invention are effective A II antagonists and therefore are useful for treating hypertension. They are also of value in the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of other diseases or therapies such as proteinuria, glomerulonephritis, glomerular sclerosis, scleroderma, diabetic nephropathy, end stage renal disease, renal transplant therapy and others. These compounds will also be useful in the treatment of left ventricular dysfunction, diabetic retinopathy, Alzheimers disease, in the enhancement of cognition, in treatment of elevated intraocular pressure, and in the enhancement of retinal blood flow. These compounds will also be useful as antidepressants and anxiolytics and in the prevention or treatment of restenosis following angioplasty. The application of the compounds of this invention for these and similar disorders will be apparent to those skilled in the art.

The usefulness of these compounds as lipid lowering agents was assessed using cholesterol absorption in a cholesterol/cholic acid-fed rat model which is described as follows. Newly arrived rats are housed for 5 days in a room with reversed light/dark cycle and fed pelleted rat chow (Purina 5001). The food is removed, and the rats are placed on a daily 4 h/day feeding schedule (beginning at 9:00 AM) with normal chow for 7 days. After acclimation (total of 12 days) and randomization based on weight, dosing with drugs and feeding of cholesterol/cholic acid is initiated. Drug solublized in vehicle (0.1 mL; olive oil, corn oil, 2% Tween 80, or carboxymethyl cellulose) is administered orally through a dosing needle immediately prior to (9:00 AM) and immediately following the 4 h feeding period. Dosing with drugs and feeding of the cholesterol/cholic acid diet is repeated for 4 days. On the morning of the 5th day, rats are sacrificed (decapitation), blood is collected and the livers are removed, weighed and stored frozen ($-80°$ C.). The animals are analyzed for total plasma cholesterol (TPC), high density lipoprotein cholesterol (HDLC, Sigma kit) and triglycerides (TG) on an Abbott Autoanalyzer. VLDL+LDL cholesterol is calculated by the difference between total and HDL cholesterol. HDL cholesterol/total cholesterol is also calculated. Typically the compounds of this invention show a 50% drop in total cholesterol at doses in the range of 100-200 mg/kg.

As illustrated above the compounds of this invention are effective lipid lowering agents and therefore are useful for treating hyperlipidemia and/or hypercholesterolemia.

Specific procedures are described in the following experimental examples. These examples are given to illustrate the invention and should not be construed as limiting the invention set forth in the appended claims.

EXPERIMENTAL

EXAMPLE 1

The preparation of 4'-[[(7-chloro-2-trifluoromethyl-4-quinazolinyl)amino]-methyl][1,1'-biphenyl]-2-carboxylic acid Part A: The preparation of 4-chloro-2-nitrobenzamide.

To 25 mL of a 2M solution of thionyl chloride in methylene chloride was added 5.0 g of 4-chloro-2-nitrobenzoic acid. The reaction mixture was refluxed for approximately 18 hours. The reaction mixture was cooled to room temperature and was added dropwise to excess 28% aqueous ammonia held at $-30°$ C. Additional $CH_2Cl_2$ (50 mL) was added and the organic layer was recovered, dried over anhydrous magnesium sulfate, filtered and evaporated. The residue was taken up in ethyl acetate, washed with brine, dried over anhydrous magnesium sulfate, filtered and evaporated to yield the product as a tan powder (4.92 g, 99%): $^1$H NMR (DMSO-$d_6$, 300 MHz) δ8.25 (bs, 1H), 8.14 (m, 1H), 7.87 (m, 1H), 7.78 (bs, 1H), 7.68 (m, 1H).

Part B: The preparation of 4-chloro-2-aminobenzamide.

To 70 mL of glacial acetric acid was added 4-chloro-2-nitrobenzamide (2.0 g) and iron powder (2.8 g). The reaction mixture was heated at 90° C. for 2 hours. The reaction mixture was cooled to room temperature and all solvents were removed by evaporation. The residue was taken up in a mixture of ethyl acetate and saturated aqueous sodium carbonate. This mixture was filtered through celite and the organic phase was recovered and washed with brine. The organic phase was then dried over anhydrous magnesium sulfate, filtered and evaporated to yield 1.65 g of the product as a buff powder (97%): $^1$H NMR (DMSO-d$_6$, 300 MHz) δ7.75 (bs, 1H), 7.55 (d, 1H), 7.15 (bs, 1H), 6.82 (bs, 2H), 6.73 (d, 1H), 6.45 (dd, 1H).

Part C: The preparation of 7-chloro-2-trifluoromethyl-4-quinazalone.

Trifluoroacetamide (1.64 g) and 4-chloro-2-aminobenzamide (1.65 g) were mixed intimately and were heated under nitrogen to 180° C. for 4 hours. The reaction solution was cooled to room temperature and solidified. The resulting solid was recrystalized from absolute ethanol to yield 0.51 g (21%) of the product as a buff powder: $^1$H NMR (DMSO-d$_6$, 300 MHz) δ13.78 (bs, 1H), 8.20 (m, 1H), 7.92 (d, 1H), 7.75 (m, 1H).

Part D: The preparation of 4,7-dichloro-2-trifluoromethylquinazoline.

To a mixture of POCl$_3$ (5 mL) and dimethyl aniline (0.5 mL) was added 0.51 g of 7-chloro-2-trifluoromethyl-4-quinazalone. The reaction was refluxed for 3½ hours, cooled to room temperature and quenched into an ice cold mixture of diethyl ether and water. The organic layer was washed with brine, dried over magnesium sulfate, filtered and evaporated to yield a yellow brown solid (0.52 g, 94%): $^1$H NMR (DMSO-d$_6$, 300 MHz) δ8.43 (m, 2H), 8.10 (m, 1H).

Part E: The preparation of 4'-[[(7-chloro-2-trifluoromethyl-4-quinazolinyl)amino]methyl][1,1'-biphenyl]-2-carboxylic acid.

To 25 mL of tetrahydrofuran were added sodium acetate (0.5 g), 4,7-dichloro-2-trifluoromethyl quinazoline (0.33 g) and 4' aminomethyl (1,1'-biphenyl)-2-carboxylic acid. The reaction mixture was stirred at 40°-50° C. for approximately 18 hours. All the THF was removed by evaporation and the residue was partitioned between ethyl acetate and brine. The organic layer was dried over anhydrous magnesium sulfate, filtered and evaporated. The resulting residue was purified by silica chromatography to yield 0.54 g (98%) of the title product as an off-white powder. The compound was characterized as the sodium salt: $^1$H NMR (DMSO-d$_6$, 300 MHz) δ10.20 (s, 1H), 8.52 (d, J=9 Hz, 1H), 7.87 (d, J=2 Hz, 1H), 7.63 (dd, J=2.2, 8.8 Hz, 1H), 7.38 (m, 5H), 7.22 (m, 3H), 4.74 (d, J=5.6 Hz); negative FAB MS m/e 456(M-Na). Anal. calcd for C$_{23}$H$_{14}$F$_3$ClNNaO$_2$.1.5H$_2$O: C, 54.50; H, 3.38; N, 8.29. Found: C, 54.35; H, 3.45; N, 8.46.

EXAMPLE 2

The preparation of 4'-[[(2,6-dichloro-4-quinazolinyl)amino]methyl][1,1'-biphenyl]-2-carboxylic acid methyl ester Part A: Preparation of 5-chloro-2-aminobenzamide.

To 5-chloro-2-nitrobenzamide (2.0 g) (prepared according to the procedure described in Example 1, Part A) was added 50 mL of glacial acetic acid. This solution was heated to 90° C. and iron powder (2.8 g) was added in small portions over 15 minutes. When addition was complete the reaction mixture was stirred at 90°-100° C. After 2 hours the reaction was cooled to room temperature and was evaporated to dryness. The resulting residue was partitioned between ethyl acetate and aqueous sodium carbonate. This brown slurry was filtered and the ethyl acetate layer was recovered and washed with brine, dried over anhydrous magnesium sulfate, filtered and evaporated to dryness to yield 1.7 g (100%) of a buff powder: $^1$H NMR (DMSO-d$_6$, 300 MHz) δ7.83 (bs, 1H), 7.59 (d, 1H), 7.17 (bs, 1H), 7.14 (dd, 1H), 6.70 (m, 3H).

Part B: The preparation of 6-chloro-2,4-quinazolinedione.

Urea (2.64 g) and 5-chloro-2-amino benzamide (3.75 g) were dissolved in 100 mL of pyridine. To this solution was added 10% HCl (aq.) (6 drops) and the resulting solution was refluxed for 12-18 hours. The reaction mixture was evaporated to dryness and the resulting residue was suspended in 125 mL of water. The pH of the suspension was adjusted to 6 with dilute hydrochloric acid and the solid was recovered by filtration. The filter cake was washed well with water and was dried to yield 3.27 g of buff powder (76%): $^1$H NMR (DMSO-d$_6$, 300 MHz) δ11.45 (s, 1H), 11.25 (s, 1H), 7.81 (d, 1H), 7.66 (dd, 1H), 7.18 (d, 1H).

Part C: The preparation of 2,4,6-trichloroquinazoline.

A mixture of 6-chloro-2,4-quinazolinedione (3.27 g) in 30 mL of phosphorous oxychloride and 1.5 mL of dimethylaniline was refluxed for 4½ hours. The reaction was cooled to room temperature and was poured into a 0° C. mixture of 300 mL of diethyl ether and 300 mL of water. The ether layer was washed with brine, dried over anhydrous magnesium sulfate, filtered and evaporated to dryness to yield 3.54 g of a brown/yellow solid (91%): $^1$H NMR (DMSO-d$_6$, 300 MHz) δ8.325 (m, 1H), 8.20 (m, 1H), 8.085 (m, 1H).

Part D: The preparation of 4'-[[(2,6-dichloro-4-quinazolinyl)amino]methyl][1,1'-biphenyl]-2-carboxylic acid methyl ester.

A mixture of sodium acetate (0.44 g), 2,4,6-trichloroquinazoline, (0.42 g) and 4'-amino methyl(1,1'-biphenyl)-2-carboxylic acid methyl ester, hydrochloride (0.47 g) in 10 mL of THF was stirred at room temperature for 5 days. At that time all solvents were removed by evaporation and the residue was partitioned between ethyl acetate and brine. The ethyl acetate fraction was dried over anhydrous magnesium sulfate, filtered and evaporated. The crude material was purified using silica gel chromatography to yield 0.45 g (58%) of the product as a yellow powder (m.p.=98°-102° C.); $^1$H NMR (DMSO-d$_6$, 400 MHz) δ9.40 (t, J=5.9 Hz, 1H), 8.50 (d, J=2.2 Hz, 1H), 7.83 (dd, J=2.3, 8.9 Hz, 1H), 7.71 (dd, J=1.1, 7.7 Hz, 1H), 7.66 (d, J=8.9 Hz, 1H), 7.59 (dt, J=1.4, 7.6 Hz, 1H), 7.46 (m, 1H), 7.40 (m, 3H), 7.26 (m, 2H), 4.79 (d, J=5.7 Hz, 2H), 3.58 (s, 3H); EI MS m/e 437(M+). Anal. calcd for C$_{23}$H$_{17}$Cl$_2$N$_3$O$_2$: C, 63.03; H, 3.91; N, 9.59. Found: C, 63.13; H, 3.95; N, 9.31.

EXAMPLE 3

The preparation of 4'-[[(2,6-dichloro-4-quinazolinyl)amino]methyl][1,1'-biphenyl]-2-carboxylic acid A mixture of sodium acetate (0.56 g), 2,4,6-trichloroquinazoline (0.40 g) and 4'-aminomethyl (1,1'-biphenyl)-2-carboxylic acid (0.43 g) was stirred at room temperature in 10 mL of THF for 5 days. All solvents were removed by evaporation and the resulting residue was partitioned between ethyl acetate and brine. The ethyl acetate fraction was dried over anhydrous magnesium sulfate, filtered and evaporated. The crude material was purified using silica gel chromatography to yield 0.15 g (21%) of an off white solid (m.p.=210°-240° C.): $^1$H NMR (DMSO-d$_6$, 400 MHz) δ9.45 (t, J=6.2 Hz, 1H), 8.52 (d, J=2.3 Hz, 1H), 7.83

(dd, J=2.3, 8.9 Hz, 1H), 7.66 (m, 2H), 7.49 (m, 1H), 7.35 (m, 7H), 4.77 (d, J=5.2 Hz); negative FAB MS m/e 422(M-H). Anal. calcd for $C_{22}H_{15}Cl_2N_3O_2$: C, 62.28; H, 3.56; N, 9.90. Found: C, 62.44; H, 3.52; N, 9.95.

EXAMPLE 4

The preparation of 4'-[[(2-chloro-4-quinazolinyl)amino]methyl][1,1'-biphenyl]-2-carboxylic acid methyl ester Sodium acetate (0.65 g), 2,4-dichloroquinazoline (0.52 g) and 4'-aminomethyl[1,1'-biphenyl]-2-carboxylic acid methyl ester (0.73 g) were suspended in 25 mL of tetrahydrofuran. The reaction was stirred at room temperature for approximately 18 hours at which time the solvents were evaporated. The residue was loaded onto a silica gel column and the desired product was eluted with ethyl acetate/hexane (1:1). The yield was 0.75 g (71%) (m.p.=75°-90° C.): $^1$H NMR (DMSO-$d_6$, 300 MHz) δ9.30 (t, J=6 Hz, 1H), 8.33 (d, J=8.1 Hz, 1H), 7.81 (m, 1H), 7.71 (m, 1H), 7.60 (m, 3H), 7.45 (m, 4H), 7.25 (d, J=8.1 Hz, 2H), 4.80 (d, J=5.8 Hz, 2H), 3.58 (s, 3H); positive FAB MS m/e 404(MH). Anal. calcd for $C_{23}H_{18}ClN_3O_2$: C, 68.40; H, 4.49; N, 10.40. Found: C, 68.09; H, 4.57; N, 10.10.

EXAMPLE 5

The preparation of 4'-[[(2-chloro-4-quinazolinyl)amino]methyl][1,1'-diphenyl]-2-carboxylic acid Procedure 1

To a solution of 0.245 g of 4'-[[(2-chloro-4-quinazolinyl)amino]methyl][1,1'-biphenyl]-2-carboxylic acid, methyl ester in 10 mL of 1:1 MeOH:Dioxane was added. 3.6 mL of 0.5N aqueous sodium hydroxide. The reaction solution was stirred at room temperature for 10 days. All solvents were removed by evaporation and the residue was neutralized with hydrochloric acid. The resulting solid was filtered off and washed well with water. This was purified using silica gel chromatography to yield 0.074 g of the desired product (m.p.=223°-233° C.): $^1$H NMR (DMSO-$d_6$, 400 MHz) δ12.70 (bs, 1H), 9.38 (t, J=6.1 Hz, 1H), 8.34 (d, J=7.5 Hz, 1H), 7.83-7.22 (m, 11H), 4.80 (d, J=5.8 Hz, 2H); negative FAB MS m/e 388(M-H). Anal. calcd for $C_{22}H_{16}ClN_3O_2$: C, 67.78; H, 4.14; N, 10.78. Found: C, 67.91; H, 4.34; N, 10.68.

Procedure 2

To 50 mL of THF were added 0.46 g of 2,4-dichloroquinazoline, 0.58 g of 4-(aminomethyl)(1,1'-biphenyl)-2-carboxylic acid and 0.76 g of sodium acetate. The reaction mixture was stirred at room temperature for 2 days. At that time all solvents were evaporated and the resulting residue was partitioned between ethyl acetate and brine. The organic layer was dried over anhydrous magnesium sulfate, filtered and evaporated to yield 0.44 g (49%) of the desired product. This product was identical to that obtained from procedure 1 described above.

EXAMPLE 6

The preparation of N-[[2'-(1H-tetrazol-5-yl)[1,1'-biphenyl]-4-yl]methyl]-2-trifluoromethyl-4-quinazolinamine Part A: The preparation of 2-trifluoromethyl-4-quinazolone.

To 12 g of trifluoroacetamide was added 3.34 g of 2-aminobenzamide. The mixture was mixed intimately and was heated to 160° C. for 5 hours. The reaction mixture was cooled and the resulting solid was recrystallized from ethanol to yield 3.7 g (70.3%) of the desired product: $^1$H NMR (DMSO-$d_6$, 300 MHz) δ13.80 (bs, 1H), 8.21 (dd, 1H), 7.95 (m, 1H), 7.82 (m, 1H), 7.65 (m, 1H).

Part B: The preparation of 4-chloro-2-trifluoromethyl quinazoline.

To 20 mL of phosphorous oxychloride was added 3.02 g of 2-trifluoromethyl-4-quinazolone and 2 mL of dimethylaniline. The resulting mixture was heated at reflux for 4½ hours and then cooled to room temperature. The reaction was quenched into a 0° C. mixture of diethyl ether and water. The organic layer was recovered, washed with brine, dried over anhydrous magnesium sulfate, filtered and evaporated to yield 3.30 g of the desired product as a yellow/brown solid: $^1$H NMR (DMSO-$d_6$, 300 MHz) δ8.43 (m, 1H), 8.29 (m, 2H), 8.08 (m, 1H).

Part C: The preparation of N-[[2'-(1H-tetrazol-5-yl)[1,1'-biphenyl]-4-yl]methyl]-2-trifluoromethyl-4-quinazolinamine.

Sodium acetate (1.27 g), 4-chloro-2-trifluoromethyl-quinazoline (0.72 g) and N-[[2'-(1H-tetrazol-5-yl)[1,1'-biphenyl]-4-yl]methyl]amine (0.78 g) were added to 25 mL of THF. The resulting suspension was stirred at 40°-50° C. for 72 hours. All the THF was evaporated and the resulting residue was partitioned between ethyl acetate and brine. The organic layer was dried over anhydrous magnesium sulfate, filtered and evaporated. The residue was purified on silica chromatography to yield 0.97 g (70%) of the desired product. The compound was characterized as the potassium salt: $^1$H NMR (DMSO-$d_6$, 400 NHz) δ9.39 (t, J=5.9 Hz, 1H), 8.39 (d, J=8.5 Hz, 1H), 7.85 (m, 2H), 7.66 (m, 1H), 7.51 (m, 1H), 7.33 (m, 3H), 7.22 (d, 8.1 Hz, 2H), 7.07 (d, 8.2 Hz, 2H); negative FAB MS m/e 484 (M-H); 446 (M-K). Anal Calcd for $C_{23}H_{15}F_3KN_3 \cdot H_2O$: C, 54.86; H, 3.40; N, 19.47. Found: C, 54.61; H, 3.30; N, 19.38.

EXAMPLE 7

The preparation of 4'-[[[2-trifluoromethyl-4-quinazolinyl]amino]methyl][1,1'-biphenyl]-2-carboxylic acid methyl ester Sodium acetate (2.34 g), 4'-aminomethyl(1,1'-biphenyl)-2-carboxylic acid, methyl ester (1.99 g) and 1.66 g of 4-chloro-2-trifluoromethylquinazoline were added to 50 mL of tetrahydrofuran. The resulting suspension was stirred at 40°-50° C. for 72 hours. All the THF was removed by evaporation and the residue was partitioned between ethyl acetate and brine. The organic layer was dried over anhydrous magnesium sulfate, filtered and evaporated. The residue was purified on silica gel chromatography to yield. 3.46 g (40%) of the desired product (M.P.=135°-142° C.): $^1$H NMR (DMSO-$d_6$, 400 MHz) δ9.43 (t, J=6 Hz, 1H), 8.41 (d, 7.9 Hz, 1H), 7.88 (m, 2H), 7.70 (m, 2H), 7.58 (m, 1H), 7.43 (m, 4H), 7.25 (m, 2H), 4.85 (d, J=5.9 Hz, 2H), 3.56 (s, 3H); positive FAB MS m/e 438 (MH). Anal Calcd for $C_{24}H_{18}F_3N_3O_2 \cdot 0.5H_2O$: C, 64.57; H, 4.29; N, 9.41. Found: C, 64.83; H, 4.02; N, 9.48.

EXAMPLE 8

The preparation of
4'-[[[2-trifluoromethyl-4-quinazolinyl]amino]methyl][1,1'-biphenyl]-2-carboxylic acid In 20 mL of dioxane/methanol (1:1) was dissolved 0.245 g of 4-[[[2-trifluoromethyl-4-quinazolinyl]amino]methyl][1,1'-biphenyl]-2-carboxylic acid methyl ester. Aqueous sodium hydroxide (10 mL, 0.1N) was added and the solution was warmed to ~40° C. for 18-24 hours. All solvents were evaporated and the residue was neutralized with hydrochloric acid (2N) and extracted into ethyl acetate. The ethyl acetate layer was dried over anhydrous magnesium sulfate, filtered and evaporated. The residue was purified on silica gel chromatography to yield 0.210 g (88%) of the product. The product was characterized as the sodium salt: $^1$H NMR (DMSO-d$_6$, 300 mHz) δ9.71 (m, 1H), 8.45 (d, J=8.1 Hz, 1H), 7.86 (m, 2H), 7.64 (m, 1H), 7.39 (m, 5H), 7.21 (m, 3H), 4.80 (d, J=5.8 Hz, 2H); positive FAB MS m/e 446 (MNa), 424 (MH). Anal Calcd for $C_{23}H_{15}F_3N_3NaO_2 \cdot 1.5H_2O$: C, 58.48; H, 3.84; N, 8.90. Found: C, 58.70; H, 3.53; N, 9.18.

EXAMPLE 9

The preparation of
2-chloro-N-[[2'-(1H-tetrazol-5-yl)[1,1'-biphenyl]-4-yl]methyl]-4-quinazolinamine To 50 mL of tetrahydrofuran were added 2,4-dichloroquinazoline (0.30 g). N-[[-2'-(1H-tetrazol-5-yl)[1,1'-biphenyl]-4-yl]methyl amine hydrochloride (0.434 g) and 2.0 g of sodium acetate. The resulting suspension was stirred at room temperature for 53 hours at which time all the THF was removed by evaporation. The residue was purified by silica gel chromatography to yield 0.234 g of the desired product. (38%). The product was characterized as its sodium salt: $^1$H NMR (DMSO-d6, 400 MHz) δ9.30 (t, J=5.9 Hz, 1H), 8.31 (d, J=7.8 Hz, 1H), 7.79 (m, 1H), 7.61 (d, J=8.4 Hz, 1H), 7.52 (m, 2H), 7.32 (m, 3H), 7.18 (d, J=8.2 Hz, 2H), 7.07 (d, J=8.2 Hz, 2H), 4.72 (d, J=5.8 Hz, 2H); negative FAB MS m/e 412 (M-Na)

The following examples were or can be prepared using the procedures described in Examples 1-9.

EXAMPLE 19

The preparation of
4'-[[(1,2-dihydro-2-oxo-4-quinazolinyl)amino]methyl][1,1'-biphenyl]-2-carboxylic acid methyl ester To 30 mL of dioxane were added 0.94 g of 4'-[[2,-chloro-4-quinazolinyl)amino]methyl][1,1'-biphenyl]-2-carboxylic acid methyl ester, 0.53 g of wet isopentanol and 0.5 mL of hydrogen chloride in dioxane (4N). The resulting solution was refluxed for 8 days at which time all solvents were removed. The residue was partitioned between ethyl acetate and saturated aqueous sodium carbonate. The organic layer was washed with brine, dried over anhydrous magnesium sulfate, filtered and evaporated. The residue was purified on silica gel chromatography to yield 0.37 g (41%) of the desired product (M.P.=140°-160° C.): $^1$H NMR (DMSO-d$_6$, 400 MHz) δ10.70 (s, 1H), 8.86 (t, J=6.0 Hz, 1H), 8.09 (d, J=8.0 Hz, 1H), 7.70 (dd, J=1.3, 7.6 Hz, 1H), 7.59 (m, 2H); 7.44 (m, 4H), 7.24 (m, 2H); 7.12 (m, 2H), 4.75 (d, J=5.8 Hz, 2H), 3.59 (s, 3H); CI MS m/e 386 (M+H). Anal. Calcd for $C_{23}H_{19}N_3O_3 \cdot 0.25H_2O$: C, 70.89; H, 5.04; N, 10.78. Found: C, 70.84; H, 4.71; N, 10.62.

EXAMPLE 20

The preparation of
4'-[[(1,2-dihydro-2-oxo-4-quinazolinyl)amino]methyl][1,1'-biphenyl]-2-carboxylic acid To a solution of 0.26 g of 4'-[[(1,2-dihydro-2-oxo-4-quinazolinyl)amino]methyl][1,1'-biphenyl]-2-carboxylic acid methyl ester in 5.0 mL of methanol was added 15 mL of 0.1N aqueous sodium hydroxide. The solution was warmed to ~90° C. for 3 days. After cooling to room temperature the solution was neutralized with 0.1N HCl and the resulting precipitate was filtered off and washed with water. After drying, the solid was purified on silica gel chromatography to yield 0.160 g (64%) of the desired product. The product was characterized as its sodium salt: $^1$H NMR (DMSO-d$_6$, 400 MHz) δ10.69 (s, 1H), 9.00 (t, J=5.8 Hz, 1H), 8.11 (d, J=8.0 Hz, 1H), 7.52 (m, 1H), 7.41 (d, J=8.2 Hz, 2H), 7.28 (m, 3H), 7.14 (m, 5H), 4.68 (d, J=5.6 Hz, 2H); negative FAB MS m/e 392 (M—H); 370 (M—Na). Anal. Calcd for $C_{22}H_{16}N_3NaO_3 \cdot 1H_2O$: C, 64.23; H, 4.41; N, 10.21. Found: C, 64.43; H, 4.19; N, 9.82.

EXAMPLE 21

The preparation of
4'-[[[2-(acetyloxy)-4-quinazolinyl]amino]methyl][1,1'-biphenyl-2-carboxylic acid methylester To a solution of 0.183 g of 4'-[[(1,2-dihydro-2-oxo-4-quinazolinyl)amino]methyl][1,1'-biphenyl]-2-carboxylic acid methyl ester in 50 mL of THF and 0.067 g of N-methylmorpholine was added 0.045 g of acetyl chloride. The reaction was stirred for 1 hour and all solvents were evaporated. The residue was partitioned between ethyl acetate and brine. The organic layer was dried over anhydrous magnesium sulfate, filtered and evaporated. The residue was purified on silica gel to yield 0.08 g of the desired product (40%) and 0.11 g of the starting material (m.p.=69°-78° C.): $^1$H NMR (DMSO-d$_6$, 400 MHz) δ9.35 (bs, 1H), 8.22 (m, 1H), 7.70 (m, 2H), 7.60 (m, 1H), 7.30-7.50 (m, 6H), 7.26 (m, 2H), 4.80 (bs, 2H), 3.60 (s, 3H), 2.59 (s, 3H); positive FAB MS m/e 428 (MH); 450 (MNa). Anal. Calcd for $C_{25}H_{21}N_3O_4 \cdot 0.5$-

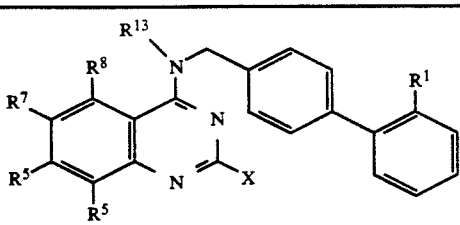

| Example | R$^{13}$ | R$^1$ | R$^8$ | R$^7$ | R$^5$ | R$^4$ | X |
|---|---|---|---|---|---|---|---|
| 10 | H | —CO$_2$H | H | OMe | OMe | H | Cl |
| 11 | H | CO$_2$H | H | H | H | H | H |
| 12 | H | CO$_2$Na | H | H | H | H | CF$_2$CF$_3$ |
| 13 | H | CO$_2$Me | H | H | H | H | CF$_2$CF$_3$ |
| 14 | H | CO$_2$H | H | H | CF$_3$ | H | CF$_3$ |
| 15 | H | 5-tetrazolyl | H | CH$_3$ | H | H | CF$_3$ |
| 16 | H | 5-tetrazolyl | H | H | H | CH$_3$ | CF$_3$ |
| 17 | H | 5-tetrazolyl | CH$_3$ | H | H | H | CF$_3$ |
| 18a | H | CO$_2$Na | H | H | H | H | CH$_3$ |
| 18b | H | 5-tetrazolyl | H | H | H | H | CH$_3$ |

H₂O: C, 68.79; H, 5.08; N, 9.63. Found: C, 68.75; H, 5.01; N, 9.48.

EXAMPLE 22

The preparation of 4'-[[[2-[(3-methylbutyl)amino]-4-quinazolinyl]amino]methyl][1,1'-biphenyl]-2-carboxylic acid methyl ester To a solution of 0.310 g of 4'-[[2-chloro-4-quinazolinyl)amino]methyl][1,1'-biphenyl]-2-carboxylic acid methyl ester in 24 mL of dioxane was added followed by 0.34 g of isopentyl amine hydrochloride. The solution was refluxed for 3 days at which time all the dioxane was evaporated. The resulting residue was taken up in ethyl acetate and washed with saturated aqueous sodium carbonate. The organic layer was washed with brine, dried over anhydrous magnesium sulfate, filtered and evaporated. The residue was purified on silica gel chromatography to yield 0.250 g (71%) of the desired product (m.p. = 52°-58° C. decomp.): ¹H NMR (DMSO-d₆, 400 MHz) δ8.42 (bs, 1H), 8.01 (m, 1H), 7.70 (m, 1H), 7.59 (m, 1H), 7.46 (m, 2H), 7.39 (m, 3H), 7.23 (m, 3H), 7.02 (m, 1H), 6.46 (bs, 1H, 1H), 4.78 (d, J=5.8 Hz, 2H), 3.58 (s, 3H), 3.27 (m, 2H), 1.6 (m, 1H), 1.40 (m, 2H), 0.86 (d, J=6.0 Hz, 6H); positive FAB MS m/e 455 (MH). Anal. Calcd for C₂₈H₃₀N₄O₂.½H₂O: C, 72.54; H, 6.74; N, 12.09. Found: C, 72.51; H, 6.66; N, 11.96.

EXAMPLE 23

The preparation of 4'-[[[2-[(3-methylbutyl)amino]-4-quinazolinyl]amino]methyl][1,1'-biphenyl]-2-carboxylic acid To 10 mL of dioxane was added 0.159 g of 4'-[[[2-[(3-methylbutyl)amino]-4-quinazolinyl]amino]methyl][1,1'-biphenyl]-2-carboxylic acid methyl ester and 2 mL of 0.5N aqueous sodium hydroxide. The resulting solution was stirred at room temperature for 72 hours. All solvents were moved and the residue was neutralized with 0.1N hydrochloric acid. The resulting precipitate was collected, washed with water and dried. (0.14 g, 93%) (M.P.=195°-205° C., decomp): ¹H NMR (DMSO-d₆, 300 MHz) δ8.43 (bs, 1H), 8.03 (m, 1H), 7.70 (m, 1H), 7.59 (m, 1H), 7.45 (m, 5H), 7.21 (m, 3H), 7.01 (m, 1H), 6.50 (bs, 1H), 4.78 (d, 2H), 3.50 (m, 2H), 1.60 (m, 1H), 1.40 (m, 2H), 0.85 (d, 6H); negative FAB MS m/e 439 (M—H). Anal. Calcd for C₂₇H₂₈N₄O₂.½HCl: C, 70.69; H, 6.26; N, 12.53. Found: C, 70.77; H, 6.20; N, 12.53.

EXAMPLE 24

The preparation of 4'-[[2,6,7-trimethoxy-4-quinazolinyl)amino]methyl][1,1'-biphenyl]-2-carboxylic acid methyl ester To a solution of 0.141 g 4'-[[2-chloro-6,7-dimethoxy-4-quinazolinyl)amino]methyl][1,1'-biphenyl]-2-carboxylic acid methyl ester in 20 mL of dry methanol was added 10 mL of hydrogen chloride in dioxane (4N). The reaction was refluxed for 5 days. All solvents were removed and the residue was purified on silica chromatography to yield 0.059 g of the desired product. (42%) (m.p.=88°-93.5° C.): ¹H NMR (DMSO-d6, 400 MHz) δ8.56 (t, J=6.1 Hz, 1H), 7.70 (m, 1H), 7.63 (s, 1H), 7.58 (m, 1H), 7.45 (m, 1H), 7.38 (m, 3H), 7.24 (m, 2H), 6.94 (s, 1H), 4.77 (d, J=5.7 Hz, 2H), 3.87 (s, 3H), 3.84 (s, 3H), 3.81 (s, 3H), 3.58 (s, 3H); positive FAB MS m/e 460 (MH). Anal. Calcd for C₂₆H₂₅N₃O₅.0.865C2H6O: C, 66.70; H, 6.09; N, 8.41. Found: C, 66.56; H, 5.80; N, 8.36.

EXAMPLE 25

The preparation of 4'-[[methyl-[2-(trifluoromethyl)-4-quinazolinyl]amino]methyl][1,1'-biphenyl]-2-carboxylic acid To a solution of 0.530 g of 4'[[[2-(trifluoro-methyl)-4-quinazolinyl]amino]methyl][1,1'-biphenyl]-2-carboxylic acid sodium salt in 10 mL of DMF was added 0.181 g of sodium hydride (60% suspension in oil). The reaction mixture was stirred at room temperature for 15 minutes at which time 2.0 mL of methyl iodide was added and stirring was continued for a further 72 hours. All solvents were removed and the residue was partitioned between ethyl acetate and brine. The organic layer was dried over anhydrous magnesium sulfate, filtered and evaporated. The residue was purified on silica gel chromatography to yield a soft glass (0.420 g). This material was dissolved in 25 mL of dioxane and 10 mL of 1N aqueous sodium hydroxide was added. The reaction solution was stirred at 40° C. for approximately 16 hours at which time all the dioxane was removed by evaporation. The desired product crystallized from the remaining water as the sodium salt. The product was recovered by filtration, washed with cold water and dried (0.405 g, 78%). This compound was characterized as its sodium salt: ¹H NMR (DMSO-d₆, 400 MHz) δ8.22 (d, J=8.5 Hz, 1H), 7.88 (m, 2H), 7.58 (m, 1H), 7.52 (m, 2H), 7.36 (m, 2H), 7.27 (m, 1H), 7.18 (m, 3H), 5.08 (s, 2H), 3.45 (s, 3H); negative FAB MS m/e 459 (M); 436 (M—Na). Anal. Calcd for C₂₄H₁₇F₃N₃NaO₂.½H₂O: C, 62.13; H, 3.80; N, 9.06. Found: C, 62.18; H, 3.85; N, 9.03.

The following examples were or can be prepared using the procedures described in Examples 20–25.

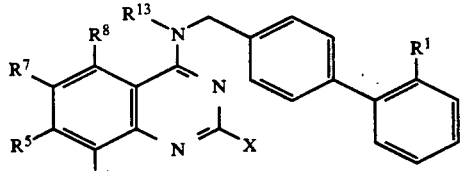

| Example | R¹³ | R¹ | R⁸ | R⁷ | R⁵ | R⁴ | X |
|---|---|---|---|---|---|---|---|
| 26 | H | —CO₂Me | H | OMe | OMe | H | HNnBu |
| 27 | H | —CO₂H | H | H | H | H | NH(CH₂)₂—OMe |
| 28 | H | —CO₂H | H | OMe | OMe | H | —NHnBu |
| 29 | H | —CO₂Me | H | OMe | OMe | H | —OH |
| 30 | H | CO₂H | H | H | H | H | —HNnBu |
| 31 | —CH₂—CO₂—Me | —CO₂—CH₂CO₂Me | H | H | H | H | CF₃ |

-continued

[Structure with R13, R8, R7, R5, R4, R1, X substituents on a biphenyl-aminomethyl-phenyl scaffold]

| Example | R13 | R1 | R8 | R7 | R5 | R4 | X |
|---------|-----|-----|----|----|----|----|----|
| 32 | —CH$_2$—CO$_2$H | CO$_2$H | H | H | H | H | CF$_3$ |

EXAMPLE 33

The preparation of 4'-[[[2-chlorothieno-[3,2-d]pyrimidin-4-yL]amino]methyl][1,1'-biphenyl]-2-carboxylic acid methyl ester Part A: The preparation of 2,4-thieno[3,2-d]pyrimidinedione.

To a solution of 4.6 g of 3-aminothiophene-2-carboxamide in 125 mL of pyridine were added 3.89 g of urea and 10 drops of 6N hydrochloric acid. The reaction was refluxed overnight and most of the pyridine was removed by evaporation. The residue was suspended in water and adjusted to pH=6 with dilute hydrochloric acid. The solid precipitate was collected by filtration, washed with water and dried to yield the product as an off white powder (3.47 g, 65%); $^1$H NMR (DMSO-d$_6$, 300 MHz) δ11.58 (s, 1H), 11.20 (s, 1H), 8.05 (d, 1H), 7.95 (d, 1H).

Part B: The preparation of 2,4-dichloro thieno[3,2-d]pyrimidine.

Phosphorous oxychloride (15 mL) was added to 1.95 g of 2,4-thieno[3,2-d]pyrimidindione. Dimethylaniline (1 mL) was added and the reaction mixture was heated to reflux for 4½ hours. After cooling to room temperature, the reaction mixture was quenched into a 0° C. mixture of diethyl ether and water. The organic layer was dried over anhydrous magnesium sulfate, filtered and evaporated to yield the product. As a brown/yellow solid (1.7 g, 71%).

Part C: The preparation of 4'-[[[2-chlorothieno-[3,2-d]pyrimidine-4-yl]amino]methyl][1,1'-biphenyl]-2-carboxylic acid methyl ester.

Sodium acetate (1.2 g), 2,4-dichlorothieno[3,2-d]pyrimidine(0.75 g) and 4'-aminomethyl(1,1'-biphenyl)-2-carboxylic acid methylester hydrochloride (1.02 g) were suspended in 40 mL of tetrahydrofuran. The reaction mixture was stirred at room temperature for 3 days at which time all the THF was removed by evaporation. The residue was partitioned between ethyl acetate and saturated aqueous sodium carbonate. The organic layer was dried over anhydrous magnesium sulfate, filtered and evaporated. The residue was purified on silica gel chromatography (ETOAc/Hexane) to yield the product as a buff powder (0.81 g, 54%) (m.p.=177°-182° C.): $^1$H NMR (DMSO-d$_6$, 400 MHz) δ8.98 (t, J=6.0 Hz, 1H), 8.19 (d, J=5.4 Hz, 1H), 7.71 (dd, J=1.1; 7.7 Hz, 1H), 7.60 (m, 1H), 7.46 (m, 1H), 7.38 (m, 4H), 7.25 (m, 2H), 4.73 (d, J=5.9 Hz, 2H), 3.58 (s, 3H); positive FAB MS m/e 410 (MH); 376 (M—Cl+H).

Anal. Calcd for C$_{21}$H$_{16}$ClN$_3$O$_2$S: C, 61.54; H, 3.93; N, 10.25. Found: C, 61.20; H, 4.03; N, 9.89.

EXAMPLE 34

The preparation of 4'-[[[2-chlorothieno-[3,2-d]pyrimidin-4-yl]amino]methyl][1,1'phenyl]-2-carboxylic acid To a solution of 0.46 g of 4'-[[[2-chlorothieno-[3,2-d]pyrimidin-4-yl]amino]methyl][1,1'-biphenyl]-2-carboxylic acid methyl][1,1'-biphenyl]-2-carboxylic acid methyl ester in 10 mL of dioxane/methanol (1:1) was added 5 mL of aqueous sodium hydroxide. This solution was stirred at room temperature for 7 days. All solvents were evaporated and the residue was neutralized with hydrochloric acid. The resulting suspension was extracted with ethyl acetate. The organic layer was dried over anhydrous magnesium sulfate, filtered and evaporated. The residue was purified on silica chromatography to yield the desired product. (0.32 g, 73%). This compound was characterized as its sodium salt: $^1$H NMR (DMSO-d$_6$, 400 MHz) δ9.08 (t, J=5.95 Hz, 1H), 8.18 (d, J=5.4 Hz, 1H), 7.20–7.40 (m, 9H), 4.69 (d, J=5.8 Hz, 2H); negative FAB MS m/e 416 (M-H); 394 (M-Na). Anal. Calcd for C$_{20}$H$_{13}$ClN$_3$NaO$_2$S.1.25 H$_2$O: C, 54.55; H, 3.55; N, 9.54. Found: C, 54.37; H, 3.37; N, 9.36.

EXAMPLE 35

The preparation of N-[[2'-(1H-tetrazol-5-yl)[1,1'-biphenyl]-4-yL]methyl]-2-(trifluoromethyl)thieno[3,2-d]pyrimidin-4-amine Part A: The preparation of 2-trifluoromethyl-4-thieno[3,2-d]pyrimidinone.

To 3.80 g of trifluoroacetamide was added 3.19 g of 3-aminothiophene-2-carboxamide. The solids were mixed intimately and heated to 180° C. for 2 hours. The reaction was cooled to room temperature and the resulting solid mass was recrystallized from ethanol to yield 1.80 g of the desired product (36%): $^1$H NMR (DMSO-d$_6$-300 MHz) δ14.00 (bs, 1H), 8.40 (d, 1H), 7.60 (d, 1H).

Part B: The preparation of 4-chloro-2-trifluoromethylthieno[3,2-d]pyrimidine.

To 20 mL of phosphorous oxychloride was added 1.8 g of 2-trifluoromethyl-4-thieno[3,2-d]pyrimidinone. Dimethylaniline (1 mL) was added and the reaction mixture was heated at reflux for 4 hours. The reaction was cooled to room temperature and quenched into a 0° C. mixture of diethyl ether and water. The organic layer was washed with brine, dried over anhydrous magnesium sulfate, filtered and evaporated to yield the product as a yellow/brown semi-solid. (1.93 g, 99%).

Part C: The preparation of N-[[2'-(1H-tetrazol-5-yl)[1,1'-biphenyl]-4-yl]methyl]-2-(trifluoromethyl)-thieno[3,2-d]pyrimidin-4-amine.

Sodium acetate (2.6 g), 4-chloro-2-trifluoromethylthieno[3,2-d]pyrimidine (1.33 g), 4'-[[2'-(1H-tetrazol- 5-yl) and [1,1'-biphenyl]methyl]amine hydrochloride (1.41 g) were suspended in 50 mL of tetrahydrofuran. The reaction was heated at reflux for 6 days at which time all solvents were removed by evaporation. The residue was eluted from a silica gel column to provide 1.19 g of pure product (47%). This compound was characterized as its potassium salt: $^1$H NMR (DMSO-$d_6$, 400 MHz) δ9.05 (m, 1H), 8.27 (d, J=5.4 Hz, 1H), 7.54 (m, 2H), 7.35 (m, 3H), 7.21 (m, 2H), 7.08 (m, 2H), 4.72 (d, J=6 Hz, 2H); negative FAB MS m/e 490 (M-H); 452 (M-K). Anal. Calcd for $C_{21}H_{13}F_3KN_7S\cdot 2.5H_2O$: C, 47.00; H, 3.38; N, 18.27. Found: C, 47.00; H, 3.62; N, 17.90.

The following examples were or can be prepared using the procedures described in Examples 33–35.

| Example | R$^{13}$ | R$^1$ | R$^5$ | R$^4$ | — | — | X |
|---|---|---|---|---|---|---|---|
| 36 | H | CO$_2$Na | H | H | — | — | CF$_3$ |
| 37 | H | 5-tetrazolyl | H | H | — | — | Cl |

EXAMPLE 38

The preparation of 4'-[[2-(pentafluoromethyl)-4-quinazolinyl]amino][1,1'-biphenyl]-2-carboxylic acid methyl ester Part A: The preparation of 4'-nitro(1,1'-biphenyl)-2-carboxylic acid methyl ester.

To a solution of 2-carboxy-4'-nitro biphenyl (5.29) in 100 mL of anhydrous methanol was added 10 mL of HCl in dioxane (4N). The reaction was heated at reflux for 16 hrs. The reaction was cooled and all solvents were removed in vacuo. The crude ester (5.65 g) was carried to the next step with no further purification.

Part B: The preparation of 4'-amino(1,1'-biphenyl)-2 carboxylic acid methyl ester.

The crude ester from part A was dissolved in 100 mL of methanol and 4.0 mL of 12N hydrochloric acid was added. Palladium on carbon (10%; 0.6 g) was added and the reaction was hydrogenated at ~50 psi for 24 hrs. The reaction was filtered and all solvents were removed in vacuo to yield a tan solid: $^1$H NMR (DMSO-$d_6$, 200 MHz) δ7.76(m, 1H), 7.60(m, 1H), 7.49(m, 1H), 7.38(m, 5H), 3.60(s, 3H).

Part C: The preparation of 4'-[[2-(pentafluoromethyl)-4-quinazolinyl]amino][1,1'-biphenyl]-2-carboxylic acid methyl ester.

Sodium acetate (4.8 g), 4-chloro-2-(pentafluoroethyl)quinazoline (1.53 g) and 1.57 g of 4'-amino (1,1'-biphenyl)-2-carboxylic acid methyl ester were stirred at 45° C. in 100 mL of tetrahydrofuran. After 72 hours all solvents were evaporated and the residue was partitioned between ethyl acetate and brine. The organic layer was dried over anhydrous magnesium sulfate, filtered and evaporated. The resulting solid was recrystallized from ethyl acetate/hexane to give 1.65 g of the desired product (64%) (M.P.=206.5°–208° C.): $^1$H NMR (DMSO-$d_6$, 400 MHz) δ10.37 (s, 1H), 8.72 (d, J=8.4 Hz, 1H), 7.97 (m, 1H), 7.83 (m, 1H), 7.72 (m, 1H), 7.62 (m, 1H), 7.48 (m, 2H), 7.35 (d, J=8.6 Hz, 2H), 3.61 (s, 3H); positive FAB MS m/e 474(MH). Anal. calcd for $C_{24}H_{16}F_5N_3O_2$: C, 60.89; H, 3.41; N, 8.88. Found: C, 61.01; H, 3.76; N, 8.86.

EXAMPLE 39

The preparation of 4'-[[2-(pentafluoromethyl)-4-quinazolinyl]amino][1,1'-biphenyl]-2-carboxylic acid To a solution of 1.0 g of 4'-[[2-(pentafluoro ethyl)-4-quinazolinyl]-amino][1,1'-biphenyl]-2-carboxylic acid methyl ester in 20 mL of dioxane was added 20 mL of aqueous sodium hydroxide. The mixture was stirred at 75° C. for 18 hours at which time all solvents were removed. The residue was partitioned between ethyl acetate and 2N hydrochloric acid. The organic layer was washed with brine, dried over anhydrous magnesium sulfate, filtered and evaporated. The residue was purified on silica gel (ethyl acetate/hexane) to yield 0.780 g of the desired product (80%). This compound was characterized as its sodium salt: $^1$H NMR (DMSO-$d_6$, 400 MHz) δ11.58 (bs, 1H), 8.97 (d, J=8.4 Hz, 1H), 7.98 (d, J=8.4 Hz, 2H), 7.91 (m, 2H), 7.60 (m, 1H), 7.48 (m, 2H), 7.41 (m, 1H), 7.26 (m, 3H); negative FAB MS m/e 480(M-H); 458(M-Na). Anal. calcd for $C_{23}H_{13}F_5N_3NaO_2\cdot 2H_2O$: C, 53.39; H, 3.31; N, 8.12. Found: C, 53.33; H, 3.47; N, 8.43.

The following example was or can be prepared using the procedures described in examples 38 and 39.

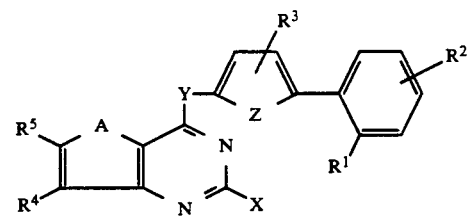

| Example | R$^{13}$ | R$^1$ | R$^8$ | R$^7$ | R$^5$ | R$^4$ | X |
|---|---|---|---|---|---|---|---|
| 40 | H | CO$_2$Na | H | H | H | H | CF$_3$ |

We claim:
1. The compounds of formula I:

wherein
A is —CR$^7$=CR$^8$—;
Z is —CR$^7$=CR$^8$—;
X is H, NR$^9$R$^{10}$, OR$^{11}$, CN, F, Cl, I, Br, perfluoroalkyl, alkyl, alkyl-OH, alkoxyalkyl, —(CH$_2$)$_n$CO$_2$R$^{11}$, —(CH$_2$)$_n$CONR$^9$R$^{10}$;
Y is NR$^{13}$, NR$^{13}$CR$^{12}$R$^{14}$, CR$^{12}$R$^{14}$NR$^{13}$;
R$^1$ is 5-tetrazolyl, CO$_2$R$^{11}$, SO$_3$H, NHSO$_2$CH$_3$, NHSO$_2$CF$_3$;
R$^2$, R$^3$, R$^4$, R$^7$, R$^8$ is H, alkyl, alkoxyalkyl, alkyl-OH, perfluoroalkyl, aralkyl, CN, NO$_2$, SO$_2$R$^{13}$, —$(CH_2)_nCO_2R^{11}$, —$(CH_2)_nCONR^9R^{10}$, $OR^{11}$, F, Cl, Br, I, $NR^9R^{10}$;

$R^5$ is alkyl, alkoxyalkyl, alkyl-OH, perfluoroalkyl, aralkyl, H, —CN, $NO_2$, $SO_2R^{13}$, —$(CH_2)_nCO_2R^{11}$, —$(CH_2)_nCONR^9R^{10}$, —OH, $OR^{11}$, F, Cl, Br, I, $NR^9R^{10}$;

$R^9$, $R^{10}$ is H, alkyl, alkoxyalkyl, alkyl-OH, perfluoroalkyl, aralkyl;

$R^{11}$ is H, alkyl, aralkyl, alkoxyalkyl;

$R^{12}$, $R^{14}$ is H, alkyl, alkoxy, alkoxyalkyl, alkyl-OH, perfluoroalkyl, aralkyl, CN, $NO_2$, $SO_2R^{13}$, —$(CH_2)_nCO_2R^{11}$, —$(CH_2)_nCONR^9R^{10}$;

$R^{13}$ is H, $OR^{11}$, alkyl, perfluoroalkyl, aralkyl, —$(CH_2)_nCO_2R^{11}$, —$(CH_2)_nCONR^9R^{10}$; wherein alkyl and alkoxy contain 1-8 carbon atoms; perfluoroalkyl contains 1-6 carbon atoms; aralkyl contains 7-12 carbon atoms or 7-12 carbon atoms substitued with fluorine, bromine or chlorine; n is 0, 1, 2 or 3 or the pharmaceutically acceptable salts, solvates and hydrates thereof.

2. The compounds of claim 1 wherein:
A is —$CR^7=CR^8$—;
Z is —$CR^7=CR^8$—;
X is H, CN, F, Cl, perfluoroalkyl, alkyl, alkyl-OH, alkoxyalkyl, —$(CH_2)_nCO_2R^{11}$, —$(CH_2)_nCONR^9R^{10}$;
Y is —$NR^{13}$, —$NR^{13}CR^{12}R^{14}$;
$R^1$ is 5-tetrazolyl, $CO_2H$, $SO_3H$, $NHSO_2CF_3$;
$R^2$, $R^3$, $R^4$, $R^7$, $R^8$=H, alkyl, alkoxyalkyl, alkyl-OH, perfluoroalkyl, aralkyl, CN, $NO_2$, $SO_2R^{13}$, —$(CH_2)_nCO_2R^{11}$, —$(CH_2)_nCONR^9R^{10}$, $OR^{11}$, F, Cl, Br, I, $NR^9R^{10}$;
$R^5$ is alkyl, alkoxy, alkoxyalkyl, alkyl-OH, perfluoroalkyl, aralkyl, H, —CN, $NO_2$, $SO_2R^{13}$, —$(CH_2)_nCO_2R^{11}$, —$(CH_2)_nCONR^9R^{10}$, —OH, $OR^{11}$, F, Cl, Br, I, $NR^9R^{10}$;
$R^9$, $R^{10}$ is H, alkyl, perfluoroalkyl, aralkyl;
$R^{11}$ is H, alkyl, aralkyl, alkoxyalkyl;
$R^{12}$, $R^{14}$ is H, alkyl, alkoxy, alkoxyalkyl, alkyl-OH, perfluoroalkyl, aralkyl, CN, $NO_2$;
$R^{13}$ is H, $OR^{11}$, alkyl, perfluoroalkyl, aralkyl, $(CH_2)_nCO_2R^{11}$, —$(CH_2)_nCONR^9R^{10}$;
wherein alkyl and alkoxy contain 1-8 carbon atoms; perfluoroalkyl contains 1-6 carbon atoms; aralkyl contains 7-12 carbon atoms or 7-12 carbon atoms substituted with fluorine, bromine or chlorine; n is 0, 1, 2 or 3 or the pharmaceutically acceptable salts, solvates and hydrates thereof.

3. The compounds of claim 2 wherein:
A is —$CR^7=CR^8$—;
Z is —$CR^7=CR^8$—;
X is H, Cl, perfluoroalkyl, alkyl;
Y is —$NR^{13}$, —$NR^{13}CR^{12}R^{14}$;
$R^1$ is 5-tetrazolyl, $CO_2H$, $SO_3H$, $NHSO_2CF_3$;
$R^2$, $R^3$, $R^4$, $R^7$, $R^8$ is H, alkyl, alkoxyalkyl, alkyl-OH, perfluoroalkyl, aralkyl, CN, $NO_2$, $SO_2R^{13}$, $OR^{11}$, F, Cl, Br, I, $NR^9R^{10}$;
$R^5$ is alkyl, alkoxyalkyl, alkyl-OH, perfluoroalkyl, aralkyl, H, —CN, $NO_2$, $SO_2R^{13}$, —OH, $OR^{11}$, F, Cl, Br, I, $NR^9R^{10}$;
$R^9$, $R^{10}$ is H, alkyl, perfluoroalkyl, aralkyl;
$R^{11}$ is H, alkyl, aralkyl, alkoxyalkyl;
$R^{12}$, $R^{14}$ is H, alkyl, alkoxy, alkoxyalkyl, alkyl-OH, perfluoroalkyl, aralkyl;
$R^{13}$ is H, $OR^{11}$, alkyl, perfluoroalkyl, aralkyl;
wherein alkyl and alkoxy contain 1-8 carbon atoms; perfluoroalkyl contains 1-6 carbon atoms; aralkyl contains 7-12 carbon atoms or 7-12 carbon atoms substituted with fluorine, bromine or chlorine; n is 0, 1, 2 or 3 or the pharmaceutically acceptable salts, solvates and hydrates thereof.

4. The compound of claim 3: 4'-[[(2-chloro-4-quinazolinyl)amino]methyl][1,1'-biphenyl]-2-carboxylic acid methyl ester or the pharmaceutically acceptable salts, solvates and hydrates thereof.

5. The compound of claim 3: 4'-[[(2-chloro-6,7-dimethoxy-4-quinazolinyl)amino]methyl][1,1'-biphenyl]-2-carboxylic acid or the pharmaceutically acceptable salts, solvates and hydrates thereof.

6. The compound of claim 3: 4'-[[[2-(butylamino)-6,7-dimethoxy-4-quinazolinyl]amino]methyl][1,1'-biphenyl]-2-carboxylic acid methyl ester or the pharmaceutically acceptable salts, solvates and hydrates thereof.

7. The compound of claim 3: 4'-[[[2-(3-methylbutylamino)-4-quinazolinyl]amino]methyl][1,1'-biphenyl]-2-carboxylic acid or the pharmaceutically acceptable salts, solvates and hydrates thereof.

8. The compound of claim 3: 4'-[[(2-chloro-4-quinazolinyl)amino]methyl][1,1'-biphenyl]-2-carboxylic acid and the pharmaceutically acceptable salts, solvates or hydrates thereof.

9. The compound of claim 3: 4'-[[(2-hydroxy-6,7-dimethoxy-4-quinazolinyl)amino]methyl][1,1'-biphenyl]-2-carboxylic acid methyl ester or the pharmaceutically acceptable salts, solvates and hydrates thereof.

10. The compound of claim 3: 4'-[[(2,6,7-trimethoxy-4-quinazolinyl)amino]methyl][1,1'-biphenyl]-2-carboxylic acid methyl ester or the pharmaceutically acceptable salts, solvates and hydrates thereof.

11. The compound of claim 3: 4'-[[(2-hydroxy-4-quinazolinyl)amino]methyl][1,1'-biphenyl]-2-carboxylic acid methyl ester or the pharmaceutically acceptable salts, solvates and hydrates thereof.

12. The compound of claim 3: 4'-[[(2,6-dichloro-4-quinazolinyl)amino]methyl][1,1'-biphenyl]-2-carboxylic acid or the pharmaceutically acceptable salts, solvates and hydrates thereof.

13. The compound of claim 3: 4'-[[(2-hydroxy-4-quinazolinyl)amino]methyl][1,1'-biphenyl]-2-carboxylic acid or the pharmaceutically acceptable salts, solvates and hydrates thereof.

14. The compound of claim 3: 4'-[(4-quinazolinylamino)methyl][1,1'-biphenyl]-2-carboxylic acid and the pharmaceutically acceptable salts, solvates or hydrates thereof.

15. The compound of claim 3: 4'-[[[2-(butylamino)-4-quinazolinyl]amino]methyl][1,1'-biphenyl]-2-carboxylic acid or the pharmaceutically acceptable salts, solvates and hydrates thereof.

16. The compound of claim 3: 4'-[[[2-(acetyloxy)-4-quinazolinyl]amino]methyl][1,1'-biphenyl]-2-carboxylic acid methyl ester or the pharmaceutically acceptable salts, solvates and hydrates thereof.

17. The compound of claim 3: 4'-[[[2-(trifluoromethyl)-4-quinazolinyl]amino]methyl][1,1'-biphenyl]-2-carboxylic acid methyl ester or the pharmaceutically acceptable salts, solvates and hydrates thereof.

18. The compound of claim 3: 4'-[[[2-(trifluoromethyl)-4-quinazolinyl]amino]methyl][1,1'-biphenyl]-2-carboxylic acid or the pharmaceutically acceptable salts, solvates and hydrates thereof.

19. The compound of claim 3: N-[[2'-(1H-tetrazol-5-yl)[1,1'-biphenyl]-4-yl]methyl]-2-(trifluoromethyl)-4- quinazolinamine or the pharmaceutically acceptable salts, solvates and hydrates thereof.

20. The compound of claim 3: 2-chloro-N-[[2'-(1H-tetrazol-5-yl)[1,1'-biphenyl]-4-yl]methyl]-4-quinazolinamine or the pharmaceutically acceptable salts, solvates and hydrates thereof.

21. The compound of claim 3: 4'-[[[7-chloro-2-(trifluoromethyl)-4-quinazolinyl]amino]methyl][1,1'-biphenyl]-2-carboxylic acid or the pharmaceutically acceptable salts, solvates an hydrates thereof.

22. The compound of claim 3: 4'-[[[2-(pentafluoroethyl)-4-quinazolinyl]amino]methyl][1,1'-biphenyl]-2-carboxylic acid or the pharmaceutically acceptable salts, solvates and hydrates thereof.

23. The compound of claim 3: 4'-[[[2,7-bis(trifluoromethyl)-4-quinazolinyl]amino]methyl][1,1'-biphenyl]-2-carboxylic acid or the pharmaceutically acceptable salts, solvates and hydrates thereof.

24. The compound of claim 3: 4'-[[(carboxymethyl)[2-(trifluoromethyl)-4-quinazolinyl]amino]methyl][1,1'-biphenyl]-2-carboxylic acid or the pharmaceutically acceptable salts, solvates and hydrates thereof.

25. The compound of claim 3: 6-methyl-N-[[2'-(1H-tetrazol-5-yl)[1,1'-biphenyl]-4-yl]methyl]-2-(trifluoromethyl)-4-quinazolinamine or the pharmaceutically acceptable salts, solvates and hydrates thereof.

26. The compound of claim 3: 8-methyl-N-[[2'-(1H-tetrazol-5-yl)[1,1'-biphenyl]-4-yl]methyl]-2-(trifluoromethyl)-4-quinazolinamine or the pharmaceutically acceptable salts, solvates and hydrates thereof.

27. The compound of claim 3: 5-methyl-N-[[2'-(1H-tetrazol-5-yl)[1,1'-biphenyl]-4-yl]methyl]-2-(trifluoromethyl)-4-quinazolinamine or the pharmaceutically acceptable salts, solvates and hydrates thereof.

28. The compound of claim 3: 4'-[[[2-(trifluoromethyl)-4-quinazolinyl]amino]methyl][1,1'-biphenyl]-2-carboxylic acid or the pharmaceutically acceptable salts, solvates and hydrates thereof.

29. The compound of claim 3: 4'-[[methyl-[2-(trifluoromethyl)-4-quinazolinyl]amino]methyl][1,1'-biphenyl]-2-carboxylic acid or the pharmaceutically acceptable salts, solvates and hydrates thereof.

30. The compound of claim 3: 2-methyl-N-[[2'-(1H-tetrazol-5-yl)[1,1'-biphenyl]-4-yl]methyl]-4-quinazolinamine or the pharmaceutically acceptable salts, solvates and hydrates thereof.

31. The compound of claim 3: 4'-[[2-(trifluoromethyl)-4-quinazolinyl]amino][1,1'-biphenyl]-2-carboxylic acid or the pharmaceutically acceptable salts, solvates and hydrates thereof.

32. The compound of claim 3: 4'-[[2-(pentafluoroethyl)-4-quinazolinyl]amino][1,1'-biphenyl]-2-carboxylic acid or the pharmaceutically acceptable salts, solvates and hydrates thereof.

33. A pharmaceutical composition containing a compound of formula I:

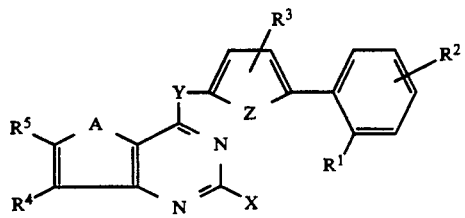

wherein

A is $-CR^7=CR^8-$;

Z is $-CR^7=CR^8-$;

X is H, $NR^9R^{10}$, $OR^{11}$, CN, F, Cl, I, Br, perfluoroalkyl, alkyl, alkyl-OH, alkoxyalkyl, $-(CH_2)_nCO_2R^{11}$, $-(CH_2)_nCONR^9R^{10}$;

Y is $NR^{13}$, $NR^{13}CR^{12}R^{14}$, $CR^{12}R^{14}NR^{13}$;

$R^1$ is 5-tetrazolyl, $CO_2R^{11}$, $SO_3H$, $NHSO_2CH_3$, $NHSO_2CF_3$;

$R^2$, $R^3$, $R^4$, $R^7$, $R^8$ is H, alkyl, alkoxyalkyl, alkyl-OH, perfluoroalkyl, aralkyl, CN, $NO_2$, $SO_2R^{13}$, $-(CH_2)_nCO_2R^{11}$, $-(CH_2)_nCONR^9R^{10}$, $OR^{11}$, F, Cl, Br, I, $NR^9R^{10}$;

$R^5$ is alkyl, alkoxyalkyl, alkyl-OH, perfluoroalkyl, aralkyl, H, $-CN$, $NO_2$, $SO_2R^{13}$, $-(CH_2)_nCO_2R^{11}$, $-(CH_2)_nCONR^9R^{10}$, $-OH$, $OR^{11}$, F, Cl, Br, I, $NR^9R^{10}$;

$R^9$, $R^{10}$ is H, alkyl, alkoxyalkyl, alkyl-OH, perfluoroalkyl, aralkyl;

$R^{11}$ is H, alkyl, aralkyl, alkoxyalkyl;

$R^{12}$, $R^{14}$ is H, alkyl, alkoxy, alkoxyalkyl, alkyl-OH, perfluoroalkyl, aralkyl, CN, $NO_2$, $SO_2R^{13}$, $-(CH_2)_nCO_2R^{11}$, $-(CH_2)_nCONR^9R^{10}$;

$R^{13}$ is H, $OR^{11}$, alkyl, perfluoroalkyl, aralkyl, $-(CH_2)_nCO_2R^{11}$, $-(CH_2)_nCONR^9R^{10}$;

wherein alkyl and alkoxy contain 1-8 carbon atoms; perfluoroalkyl contains 1-6 carbon atoms; aralkyl contains 7-12 carbon atoms or 7-12 carbon atoms substituted with fluorine, bromine or chlorine; n is 0, 1, 2 or 3 and the pharmaceutically acceptable salts, solvates and hydrates thereof in an amount effective for producing a hypotensive response in a mammal, or a pharmaceutically acceptable carrier, vehicle or diluent.

34. A method for producing hypotensive activity in a mammal by administering to that mammal a compound of formula I:

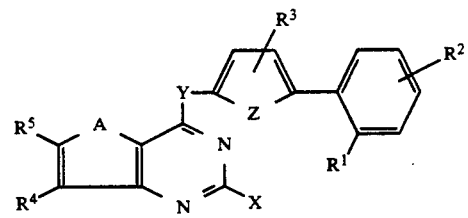

wherein

A is $-CR^7=CR^8-$;

Z is $-CR^7=CR^8-$;

X is H, $NR^9R^{10}$, $OR^{11}$, CN, F, Cl, I, Br, perfluoroalkyl, alkyl, alkyl-OH, alkoxyalkyl, $-(CH_2)_nCO_2R^{11}$, $-(CH_2)_nCONR^9R^{10}$;

Y is $NR^{13}$, $NR^{13}CR^{12}R^{14}$, $CR^{12}R^{14}NR^{13}$;

$R^1$ is 5-tetrazolyl, $CO_2R^{11}$, $SO_3H$, $NHSO_2CH_3$, $NHSO_2CF_3$;

$R^2$, $R^3$, $R^4$, $R^7$, $R^8$ is H, alkyl, alkoxyalkyl, alkyl-OH, perfluoroalkyl, aralkyl, CN, $NO_2$, $SO_2R^{13}$, $-(CH_2)_nCO_2R^{11}$, $-(CH_2)_nCONR^9R^{10}$, $OR^{11}$, F, Cl, Br, I, $NR^9R^{10}$;

$R^5$ is alkyl, alkoxyalkyl, alkyl-OH, perfluoroalkyl, aralkyl, H, $-CN$, $NO_2$, $SO_2R^{13}$, $-(CH_2)_nCO_2R^{11}$, $-(CH_2)_nCONR^9R^{10}$, $-OH$, $OR^{11}$, F, Cl, Br, I, $NR^9R^{10}$;

$R^9$, $R^{10}$ is H, alkyl, alkoxyalkyl, alkyl-OH, perfluoroalkyl, aralkyl;

$R^{11}$ is H, alkyl, aralkyl, alkoxyalkyl;

$R^{12}$, $R^{14}$ is H, alkyl, alkoxy, alkoxyalkyl, alkyl-OH, perfluoroalkyl, aralkyl, CN, $NO_2$, $SO_2R^{13}$, —$(CH_2)_nCO_2R^{11}$, —$(CH_2)_nCONR_9R^{10}$;

$R^{13}$ is H, $OR^{11}$, alkyl, perfluoroalkyl, aralkyl, —$(CH_2)_nCO_2R^{11}$, —$(CH_2)_nCONR^9R^{10}$;

wherein alkyl and alkoxy contain 1-8 carbon atoms; perfluoroalkyl contains 1-6 carbon atoms; aralkyl contains 7-12 carbon atoms or 7-12 carbon atoms substituted with fluorine, bromine or chlorine; or the pharmaceutically acceptable salts, solvates and hydrates thereof, in a hypotensively effective amount.

35. A method for treating congestive heart failure in a mammal by administering to that mammal a compound of formula I:

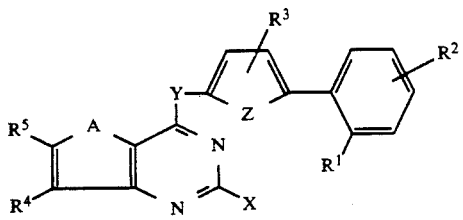

wherein
A is —$CR^7$=$CR^8$—;
Z is —$CR^7$=$CR^8$—;

X is H, $NR^9R^{10}$, $OR^{11}$, CN, F, Cl, I, Br, perfluoroalkyl, alkyl, alkyl-OH, alkoxyalkyl, —$(CH_2)_nCO_2R^{11}$, —$(CH_2)_nCONR^9R^{10}$;

Y is $NR^{13}$, $NR^{13}CR^{12}R^{14}$, $CR^{12}R^{14}NR^{13}$;

$R^1$ is 5-tetrazolyl, $CO_2R^{11}$, $SO_3H$, $NHSO_2CH_3$, $NHSO_2CF_3$;

$R^2$, $R^3$, $R^4$, $R^7$, $R^8$ is H, alkyl, alkoxyalkyl, alkyl-OH, perfluoroalkyl, aralkyl, CN, $NO_2$, $SO_2R^{13}$, —$(CH_2)_nCO_2R^{11}$, —$(CH_2)_nCONR^9R^{10}$, $OR^{11}$, F, Cl, Br, I, $NR^9R^{10}$;

$R^5$ is alkyl, alkoxyalkyl, alkyl-OH, perfluoroalkyl, aralkyl, H, —CN, $NO_2$, $SO_2R^{13}$, —$(CH_2)_nCO_2R^{11}$, —$(CH_2)_nCONR^9R^{10}$, —OH, $OR^{11}$, F, Cl, Br, I, $NR^9R^{10}$;

$R^9$, $R^{10}$ is H, alkyl, alkoxyalkyl, alkyl-OH, perfluoroalkyl, aralkyl, $R^{11}$ is H, alkyl, aralkyl, alkoxyalkyl;

$R^{12}$, $R^{14}$ is H, alkyl, alkoxy, alkoxyalkyl, alkyl-OH, perfluoroalkyl, aralkyl, CN, $NO_2$, $SO_2R^{13}$, —$(CH_2)_nCO_2R^{11}$, —$(CH_2)_nCONR^9R^{10}$;

$R^{13}$ is H, $OR^{11}$, alkyl, perfluoroalkyl, aralkyl, —$(CH_2)_nCO_2R^{11}$, —$(CH_2)_nCONR^9R^{10}$;

wherein alkyl and alkoxy contain 1-8 carbon atoms; perfluoroalkyl contains 1-6 carbon atoms; aralkyl contains 7-12 carbon atoms or 7-12 carbon atoms substituted with fluorine, bromine or chlorine; or the pharmaceutically acceptable salts, solvates and hydrates thereof in an effective amount.

* * * * *